(12) United States Patent
Matthews

(10) Patent No.: US 7,276,505 B2
(45) Date of Patent: Oct. 2, 2007

(54) IMMUNOMODULATING HETEROCYCLIC COMPOUNDS

(75) Inventor: Ian Richard Matthews, Oxfordshire (GB)

(73) Assignee: Medigene Limited (GB)

( * ) Notice: Subject to any disclaimer, the term of this patent is extended or adjusted under 35 U.S.C. 154(b) by 0 days.

(21) Appl. No.: 10/547,448

(22) PCT Filed: Mar. 10, 2004

(86) PCT No.: PCT/GB2004/001008

§ 371 (c)(1),
(2), (4) Date: Jun. 20, 2006

(87) PCT Pub. No.: WO2004/081011

PCT Pub. Date: Sep. 23, 2004

(65) Prior Publication Data

US 2007/0021428 A1    Jan. 25, 2007

(30) Foreign Application Priority Data

Mar. 14, 2003 (GB) ................................ 0305876.5
Aug. 19, 2003 (GB) ................................ 0319429.7

(51) Int. Cl.
*A01N 43/58* (2006.01)
*A01N 43/60* (2006.01)
*A61K 31/50* (2006.01)
*A61K 31/495* (2006.01)
*C07D 237/26* (2006.01)
*C07D 237/36* (2006.01)
*C07D 487/00* (2006.01)

(52) U.S. Cl. ....................... 514/248; 514/247; 544/234
(58) Field of Classification Search ..................... None
See application file for complete search history.

(56) References Cited

U.S. PATENT DOCUMENTS 4,591,589 A * 5/1986 Gasc et al. .................. 514/248

FOREIGN PATENT DOCUMENTS

WO    WO 03/004495 A    1/2003

OTHER PUBLICATIONS

Salomon, Benoit, et al., B7/CD28 Costimulation Is Essential for the Homeostasis of the CD4+CD25+ Immunoregulatory T Cells that Control Autoimmune Diabetes, Immunity, vol. 12, 431-440, Apr. 2000.*

West, Anthony R. *Solid State Chemistry and its Applications*, Wiley, New York © 1988, p. 365.*

* cited by examiner

*Primary Examiner*—James O. Wilson
*Assistant Examiner*—Erich A. Leeser
(74) *Attorney, Agent, or Firm*—Banner & Witcoff, Ltd.

(57) ABSTRACT

Compounds of formula (I) are inhibitors of CD80 and useful in immunomodulation therapy: wherein $R_1$ and $R_3$ independently represent H; F; Cl; Br; —$NO_2$; —CN; $C_1$-$C_6$ alkyl optionally substituted by F or Cl; or $C_1$-$C_6$ alkoxy optionally substituted by F; $R_4$ represents a carboxylic acid group (—COOH) or an ester thereof, or —C(=O)$NR_6R_7$, —$NR_7$C(=O)$R_6$, —$NR_7$C(=O)$OR_6$, —NHC(=O)$NR_7R_6$ or —NHC(=S)$NR_7R_6$ wherein $R_6$ represents H, or a radical of formula -(Alk)$_m$-Q wherein m is 0 or 1, Alk is an optionally substituted divalent straight or branched $C_1$-$C_{12}$ alkylene, or $C_2$-$C_{12}$ alkenylene, or $C_2$-$C_{12}$ alkynylene radical or a divalent $C_3$-$C_{12}$ carbocyclic radical, any of which radicals may contain one or more —O—, —S— or —N($R_8$)— links wherein $R_8$, represents H or $C_1$-$C_4$ alkyl, $C_3$-$C_4$ alkenyl, $C_3$-$C_4$ alkynyl, or $C_3$-$C_6$ cycloalkyl, and Q represents H; —$NR_9R_{10}$ wherein $R_9$ and $R_{10}$ independently represents H; $C_1$-$C_4$ alkyl; $C_3$-$C_4$ alkenyl; $C_3$-$C_4$ alkynyl; $C_3$-$C_6$ cycloalkyl; an ester group; an optionally substituted carbocyclic or heterocyclic group; or $R_9$ and $R_{10}$ form a ring when taken together with the nitrogen to which they are attached, which ring is optionally substituted; and $R_7$ represents H or $C_1$-$C_6$ alkyl; or when taken together with the atom or atoms to which they are attached $R_6$ and $R_7$ form an optionally substituted monocyclic heterocyclic ring having 5, 6 or 7 ring atoms; and X represents a bond or a divalent radical of formula -(Z)$_n$-(Alk)- or -(Alk)-(Z)$_n$-wherein Z represents —O—, —S— or —NH—, Alk is as defined in relation to $R_6$, and n is 0 or 1

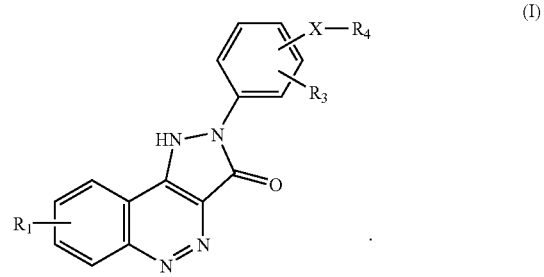

(I)

24 Claims, No Drawings

IMMUNOMODULATING HETEROCYCLIC COMPOUNDS

This application is a U.S. National Stage application of co-pending PCT application PCT/GB2004/001008 filed Mar. 10, 2004, which was published in English under PCT Article 21(2) on Sep. 23, 2004, and which claims the priority of Great Britain Patent Application No. 0305876.5, filed Mar. 14, 2003 and Great Britain Patent Application No. 0319429.7, filed Aug. 19, 2003, These applications are incorporated herein by reference in their entireties.

The present invention relates to novel heterocyclic compounds, to methods for their preparation, to compositions containing them, and to methods and use for clinical treatment of medical conditions which may benefit from immunomodulation, e.g. autoimmune disease, rheumatoid arthritis, multiple sclerosis, diabetes, asthma, transplantation, systemic lupus erythematosis and psoriasis. More particularly the present invention relates to novel heterocyclic compounds, which are CD80 antagonists capable of inhibiting the interactions between CD80 and CD28, useful for immuno-inhibition.

BACKGROUND TO THE INVENTION

The immune system possesses the ability to control the homeostasis between the activation and inactivation of lymphocytes through various regulatory mechanisms during and after an immune response. Among these are mechanisms that specifically inhibit and/or turn off an immune response. Thus, when an antigen is presented by MHC molecules to the T-cell receptor, the T-cells become properly activated only in the presence of additional co-stimulatory signals. In the absence of these accessory signals there is no lymphocyte activation and either a state of functional inactivation termed anergy or tolerance is induced, or the T-cell is specifically deleted by apoptosis.

One such co-stimulatory signal involves interaction of CD80 on specialised antigen-presenting cells with CD28 on T-cells, and this signal has been demonstrated to be essential for full T-cell activation. (Lenschow et al. (1996) *Annu. Rev. Immunol.*, 14, 233-258). It would therefore be desirable to provide compounds which inhibit this CD80/CD28 interaction.

DETAILED DESCRIPTION OF THE INVENTION

According to the present invention there is provided a compound of formula (I) or a pharmaceutically or veterinarily acceptable salt, hydrate or solvate thereof:

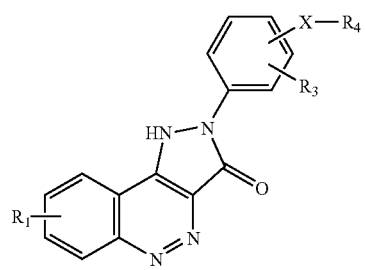

(I)

wherein
$R_1$ and $R_3$ independently represent H; F; Cl; Br; —$NO_2$; —CN; $C_1$-$C_6$ alkyl optionally substituted by F or Cl; or $C_1$-$C_6$ alkoxy optionally substituted by F;
$R_4$ represents a carboxylic acid group (—COOH) or an ester thereof, or —C(=O)$NR_6R_7$, —$NR_7$C(=O)$R_6$, —$NR_7$C(=O)$OR_6$, —NHC(=O)$NR_7R_6$ or —NHC(=S)$NR_7R_6$
wherein
$R_6$ represents H, or a radical of formula -(Alk)$_m$-Q
wherein
m is 0 or 1
Alk is an optionally substituted divalent straight or branched $C_1$-$C_{12}$ alkylene, or $C_2$-$C_{12}$ alkenylene, or $C_2$-$C_{12}$ alkynylene radical or a divalent $C_3$-$C_{12}$ carbocyclic radical, any of which radicals may contain one or more —O—, —S— or —N($R_8$)— links wherein $R_8$ represents H or $C_1$-$C_4$ alkyl, $C_3$-$C_4$ alkenyl, $C_3$-$C_4$ alkynyl, or $C_3$-$C_6$ cycloalkyl, and
Q represents H; —$NR_9R_{10}$ wherein $R_9$ and $R_{10}$ independently represents H; $C_1$-$C_4$ alkyl; $C_3$-$C_4$ alkenyl; $C_3$-$C_4$ alkynyl; $C_3$-$C_6$ cycloalkyl; an ester group; an optionally substituted carbocyclic or heterocyclic group; or $R_9$ and $R_{10}$ form a ring when taken together with the nitrogen to which they are attached, which ring is optionally substituted; and
$R_7$ represents H or $C_1$-$C_6$ alkyl; or when taken together with the atom or atoms to which they are attached $R_6$ and $R_7$ form an optionally substituted monocyclic heterocyclic ring having 5, 6 or 7 ring atoms; and
X represents a bond or a divalent radical of formula -(Z)$_n$-(Alk)- or -(Alk)-(Z)$_n$-wherein Z represents —O—, —S— or —NH—, Alk is as defined in relation to $R_6$ and n is 0 or 1.

Compounds (I) may exist in the form of tautomers, such as (I$^1$) and (I$^2$):

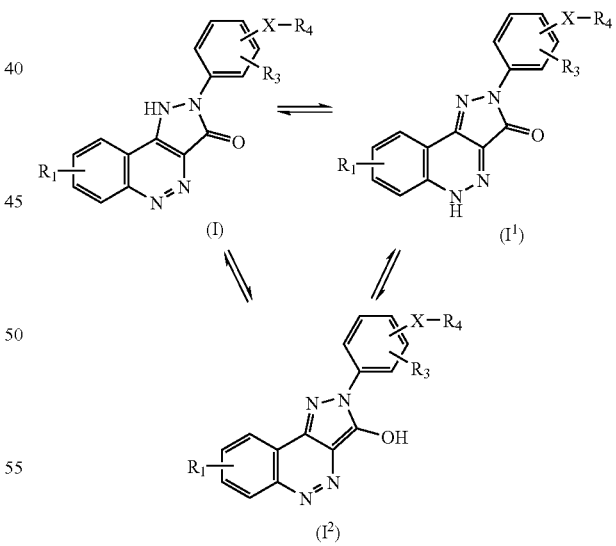

Hereafter, the compounds of the invention may be represented and referred to in any tautomeric form (I), and it is to be understood that any and all tautomeric forms of structure (I), in particular (I$^1$) and (I$^2$), are included in the invention.

Compounds of general formula (I) are CD80 antagonists. They inhibit the interaction between CD80 and CD28 and thus the activation of T cells, thereby modulating the immune response.

Accordingly the invention also includes:
(i) a compound of formula (I) or a pharmaceutically or veterinarily acceptable salt thereof for use in the treatment of conditions which benefit from immunomodulation, and in particular for immuno-inhibition.
(ii) the use of a compound of formula (I) or a pharmaceutically or veterinarily acceptable salt thereof in the manufacture of a medicament for the treatment of conditions which benefit from immunomodulation, and in particular for immuno-inhibition.
(iii) a method of immunomodulation, and in particular immuno-inhibition, in mammals, including humans, comprising administration to a mammal in need of such treatment an immunomodulatory effective dose of a compound of formula (I) or a pharmaceutically or veterinarily acceptable salt thereof.
(iv) a pharmaceutical or veterinary composition comprising a compound of formula (I) or a pharmaceutically or veterinarily acceptable salt thereof together with a pharmaceutically or veterinarily acceptable excipient or carrier.

Conditions which Benefit from Immunomodulation Include:
Acute disseminated encephalomyelitis
Adrenal insufficiency
Allergic angiitis and granulomatosis
Amylodosis
Ankylosing spondylitis
Asthma
Autoimmune Addison's disease
Autoimmune alopecia
Autoimmune chronic active hepatitis
Autoimmune haemolytic anaemia
Autoimmune Neutrogena
Autoimmune thrombocytopenic purpura
Behcet's disease
Cerebellar degeneration
Chronic active hepatitis
Chronic inflammatory demyelinating polyradiculoneuropathy
Chronic neuropathy with monoclonal gammopathy
Classic polyarteritis nodosa
Congenital adrenal hyperplasia
Cryopathies
Dermatitis herpetiformis
Diabetes
Eaton-Lambert myasthenic syndrome
Encephalomyelitis
Epidermolysis bullosa acquisita
Erythema nodosa
Gluten-sensitive enteropathy
Goodpasture's syndrome
Guillain-Barre syndrome
Hashimoto's thyroiditis
Hyperthyroidism
Idiopathic hemachromatosis
Idiopathic membranous glomerulonephritis
Isolated vasculitis of the central nervous system
Kawasaki's disease
Minimal change renal disease
Miscellaneous vasculitides
Mixed connective tissue disease
Multifocal motor neuropathy with conduction block
Multiple sclerosis
Myasthenia gravis
Opsoclonus-myoclonus syndrome
Pemphigoid
Pemphigus
pernicious anaemia
Polymyositis/dermatomyositis
Post-infective arthritides
Primary biliary sclerosis
Psoriasis
Reactive arthritides
Reiter's disease
Retinopathy
Rheumatoid arthritis
Sclerosing cholangitis
Sjogren's syndrome
Stiff-man syndrome
Subacute thyroiditis
Systemic lupus erythematosis
Systemic necrotizing vasculitides
Systemic sclerosis (scleroderma)
Takayasu's arteritis
Temporal arteritis
Thromboangiitis obliterans
Type I and type II autoimmune polyglandular syndrome
Ulcerative colitis
Uveitis
Wegener's granulomatosis As used herein, the term "ester" refers to a group of the form —COOR, wherein R is a radical notionally derived from the alcohol ROH. Examples of ester groups include the physiologically hydrolysable esters such as the methyl, ethyl, n- and iso-propyl, n-, sec- and tert-butyl, and benzyl esters.

As used herein the term "alkylene" refers to a straight or branched alkyl chain having two unsatisfied valencies, for example —$CH_2$—, —$CH_2CH_2$—, —$CH_2CH_2CH_2$—, —CH($CH_3$)$CH_2$—, —CH($CH_2CH_3$)$CH_2CH_2CH_2$—, and —C($CH_3$)$_3$.

As used herein the term "alkenylene" refers to a straight or branched alkenyl chain having two unsatisfied valencies, for example —CH=CH—, —$CH_2$CH=CH—, —C($CH_3$)=CH—, and —CH($CH_2CH_3$)CH=CH$CH_2$—.

As used herein the term "alkynylene" refers to a straight or branched alkynyl chain having two unsatisfied valencies, for example —C≡C—, —$CH_2$C≡C—, and —CH($CH_2CH_3$)C≡C$CH_2$—.

Unless otherwise specified in the context in which it occurs, the term "substituted" as applied to any moiety herein means substituted with at least one substituent, selected from, for example, ($C_1$-$C_6$)alkyl, ($C_1$-$C_6$)alkenyl, ($C_2$-$C_6$)alkynyl, fluoro-substituted($C_1$-$C_6$)alkyl, fluoro-substituted($C_1$-$C_6$)alkenyl, fluoro-substituted($C_2$-$C_6$)alkynyl, ($C_1$-$C_6$)alkoxy and fluoro-substituted($C_1$-$C_6$)alkoxy (including the special case where a ring is substituted on adjacent ring C atoms by alkylenedioxy such as methylenedioxy or ethylenedioxy), ($C_1$-$C_6$)alkylthio, phenyl, benzyl, phenoxy, benzyloxy, hydroxy, mercapto, amino, fluoro, chloro, bromo, cyano, nitro, oxo, —COOH, —$SO_2$OH, —$CONH_2$, —$SO_2NH_2$, —$COR^A$, —$COOR^A$, —$SO_2OR^A$, —$NHCOR^A$, —$NHSO_2R^A$, —$CONHR^A$, —$SO_2NHR^A$, —$NHR^A$, —$NR^AR^B$, —$CONR^AR^B$ or —$SO_2NR^AR^B$ wherein $R^A$ and $R^B$ are independently a ($C_1$-$C_6$)alkyl or ($C_2$-$C_6$)alkoxy group or a monocyclic carbocyclic or heterocyclic group of from 5-7 ring members, or $R^A$ and $R^B$ form a ring when taken together with the nitrogen to which they are attached. In the case where "substituted" means substituted by phenyl, benzyl, phenoxy, or benzyloxy, the phenyl ring thereof may itself be substituted with any of the foregoing, except phenyl, benzyl, phenoxy, or benzyloxy.

As used herein the term "aryl" refers to a mono-, bi- or tri-cyclic carbocyclic aromatic radical, and to two such radicals covalently linked to each other, Illustrative of such radicals are phenyl, biphenyl and napthyl.

As used herein the unqualified term "carbocyclyl" or "carbocyclic" includes aryl, cycloalkyl and cycloalkenyl and refers to a ring system (monocyclic, bicyclic, tricyclic or bridged) whose ring atoms are all carbon.

As used herein the unqualified term "cycloalkyl" refers to a carbocyclic ring system which contains only single bonds between ring carbons.

As used herein the unqualified term "cycloalkenyl" refers to a carbocyclic ring system which contains at least one double bond between a pair of ring carbons.

As used herein the term "heteroaryl" refers to a mono-, bi- or tri-cyclic aromatic radical containing one or more heteroatoms selected from S, N and O. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in particular means a mono-, bi- or tri-cyclic or bridged non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, tetrahydrofuranyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, tetrahydropyranyl, quinuclidinyl, isoxazolyl, benzimidazolyl, methylenedioxyphenyl, ethylenedioxyphenyl, maleimido and succinimido groups.

Some compounds of the invention contain one or more chiral centres because of the presence of asymmetric carbon atoms. The presence of asymmetric carbon atoms gives rise to stereoisomers or diastereoisomers with R or S stereochemistry at each chiral centre. The invention includes all such stereoisomers and diastereoisomers and mixtures thereof.

Salts of salt forming compounds of the invention include physiologically acceptable acid addition salts and base salts Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Methods

Compounds of the invention wherein $R_4$ represents an amide group —C(=O)NR$_6$R$_7$ may be prepared by reaction of the appropriate amine HNR$_6$R$_7$ with a compound of formula (II) to amidate the carboxylic acid group:

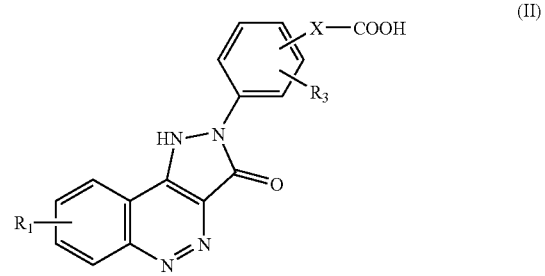

(II)

the symbols $R_1$, $R_3$, X, $R_6$ and $R_7$ being as defined in relation to formula (I) above.

Compounds (II) (ie compounds (I) of the invention wherein $R_4$ is a carboxylic acid group) may be prepared by reaction of a compound of formula (III) with a hydrazine of formula (IV):

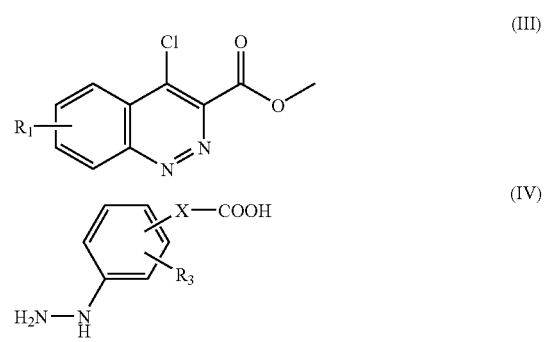

(III)

(IV)

This reaction may result in the preparation of a mixture of the position isomers (IIA) and (IIB):

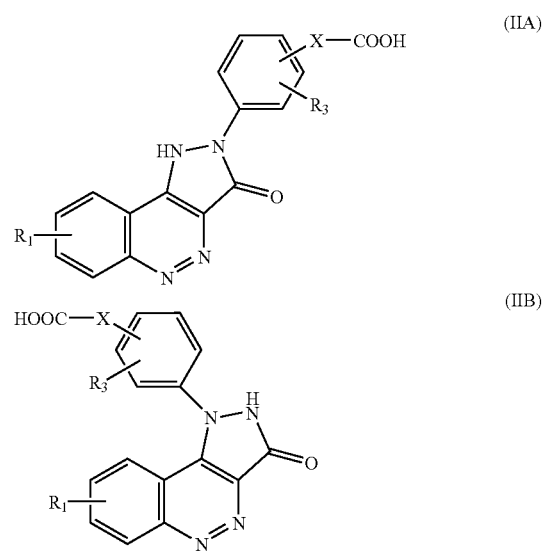

(IIA)

(IIB)

from which the desired isomer (IIA) may be separated.

Compounds (I) wherein $R_4$ is an ester or amide group may also be prepared from intermediate (III) by reaction with the appropriate hydrazine (IVA)

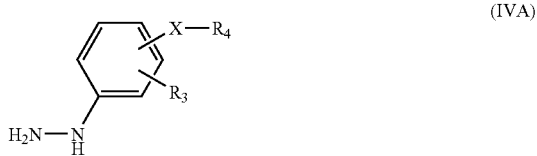
(IVA)

wherein $R_4$ is an ester or amide group. Again the reaction may result in a mixture of the ester or amide analogues of the carboxylic acids (IIA) and (IIB), from which the desired ester or amide isomer (I) may be separated. Alternatively, the carboxylic acid compound (II) may simply be esterified, or amidated.

Compounds (I) wherein $R_4$ is a "reverse amide" group —$NR_7C(=O)R_6$ may be prepared by Curtius rearrangement (see Ninomiya, K.; Shioiri, T.; Yamada, S. Tetrahedron (1974), 30(14), 2151-7) of the carboxylic acid (II) to the isocyanate (V)

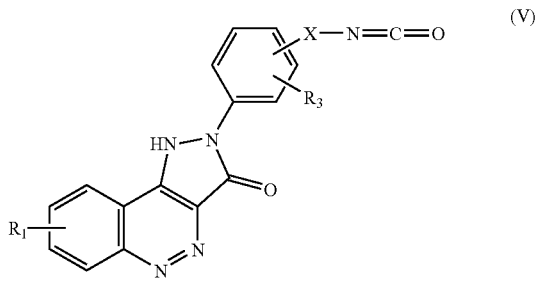
(V)

followed by hydrolysis of the isocyanate group to an amino group and acylation of the amino group with, for example, the acid chloride $Cl—C(=O)R_6$. In cases where $R_7$ is not hydrogen, the $R_7$ substituent may be introduced after the isocyanate reduction step or after the acylation step.

In an alternative route to the "reverse amide" ($R_4$=$NR_7C(=O)R_6$) compounds of the invention, a compound of structure (V) in which the isocyanate moiety is replaced by a nitro group may be reduced to the corresponding amine, which may then be acylated to form the desired reverse amide.

Compounds (I) wherein $R_4$ is a urea group —$NHC(=O)NHR_6$ or thiourea group —$NHC(=S)NHR_6$ may also be prepared from the isocyanate (V) or the corresponding isothiocyanate by reaction with the appropriate amine $H_2NR_6$.

Compounds (I) wherein $R_4$ is a carbamate group —$NR_7C(=O)OR_6$ may be prepared by the reaction of the isocyanate with an appropriate alcohol $R_6OH$.

Further details of the synthetic methods for the preparation of compounds (I) of the invention, and intermediates such as (III), may be found in the examples herein.

In the Compounds of the Invention:

The radical $R_4X$— is preferably in the 4-position of the phenyl ring.

X may be, for example a bond, or a —$CH_2$— or —$CH_2CH_2$— radical. A bond is presently preferred.

$R_3$ may be, for example, H, F, Cl, methyl, methoxy, or methylenedioxy. Currently it is preferred that $R_3$ is H.

$R_1$ may be, for example, H, F, Cl, methyl, methoxy, or methylenedioxy. Currently it is preferred that $R_1$ be hydrogen or fluoro, particularly in the 6-position of the 3-oxo-1,3-dihydro-2H-pyrazolo[4,3-c]cinnolin-2-yl ring system.

$R_4$ represents a carboxylic acid group (—COOH) or an ester thereof, or —$C(=O)NR_6R_7$, —$NR_7C(=O)R_6$, —$NR_7C(=O)OR_6$ or —$NHC(=O)NHR_6$, all as defined above.

When $R_4$ is an ester group, examples include those of formula —COOR wherein R is methyl, ethyl n- or iso-propyl, n-, sec- or tert-butyl, or benzyl ester.

$R_6$, when present, represents H, or a radical of formula -(Alk)$_m$-Q wherein m, Alk and Q being as defined above. When m is 1, Alk may be, for example a straight or branched $C_1$-$C_6$ alkylene radical, such as —$CH_2$—, —$CH_2CH_2$—, —$CH_2CH_2CH_2$—, and —$CH_2CH(CH_3)CH_2$—. Alk may also be, for example, a divalent cyclopropylene, cyclopentylene or cyclohexylene radical. The radical Alk may be optionally substituted by, for example, OH, oxo, $CF_3$, methoxy or ethoxy. The radical Alk may optionally contain a hetero atom, for example in the form of an ether, thioether or amino linkage.

The group Q may represent, for example, hydrogen; —$NR_9R_{10}$ wherein $R_9$ and $R_{10}$ may be the same or different and selected from hydrogen, methyl, ethyl, n- or isopropyl or tert-butyl; an ester group for example a methyl, ethyl or benzyl ester; or an optionally substituted aryl, aryloxy, cycloalkyl, cycloalkenyl or heterocyclic group, for example phenyl, phenoxy, cyclopentyl, cyclohexyl, furyl, thienyl, quinuclidinyl, piperidyl, or piperazinyl group.

$R_7$ when present represents H or $C_1$-$C_6$ alkyl, for example methyl, ethyl n- or iso-propyl, n-, sec- or tert-butyl; or when taken together with the atom or atoms to which they are attached $R_6$ and $R_7$ form a monocyclic heterocyclic ring having 5, 6 or 7 ring atoms.

Especially preferred are the cases where $R_4$ represents —$C(=O)NR_6R_7$ or —$NHC(=O)NR_7R_6$ wherein $R_7$ is hydrogen and $R_6$ represents a radical of formula -(Alk)$_m$-Q wherein m is 1 and the divalent radical Alk contains 3 or 4 carbon atoms and is unsubstituted, and Q represents —$NR_9R_{10}$ wherein $R_9$ and $R_{10}$ independently represents H; $C_1$-$C_4$ alkyl; $C_3$-$C_4$ alkenyl; $C_3$-$C_4$ alkynyl; $C_3$-$C_6$ cycloalkyl; an ester group; an optionally substituted carbocyclic or heterocyclic group; or form a ring when taken together with the nitrogen to which they are attached, which ring is optionally substituted.

A specific preferred subset of compounds of the invention has formula (IC):

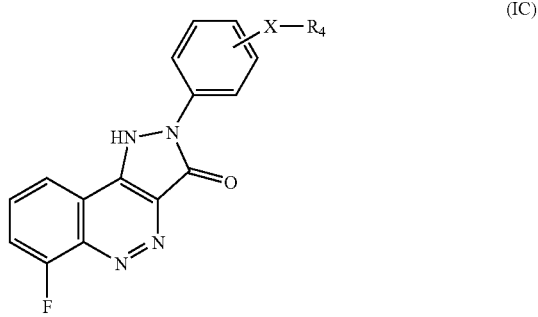
(IC)

wherein X and $R_4$ are as specified above. In this subset, the radical $R_4X$— may be in the 4-position of the phenyl ring. This subset includes in particular, compounds wherein X is a bond and $R_4$ is —C(=O)$NR_6R_7$ wherein $R_6$ and $R_7$ are as specified above. For example, in such compounds $R_6$ may be quinuclidinyl and $R_7$ hydrogen.

Specific compounds of the invention include those of the Examples herein.

A preferred compound of the invention is 4-(6-fluoro-3-oxo-1,3-dihydro-pyrazolo[4,3-c]cinnolin-2-yl)-N-(2,2-difluoro-ethyl)-benzamide, of formula (A)

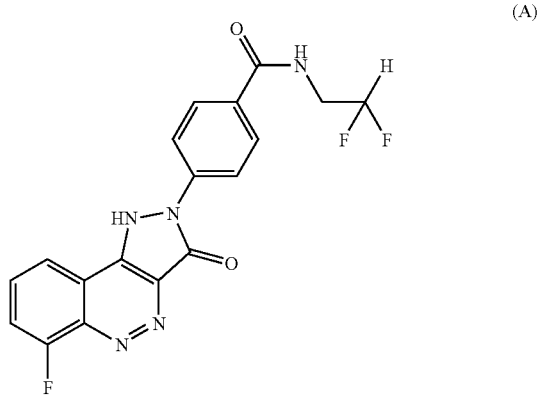

(A)

or a pharmaceutically or veterinarily acceptable salt, hydrate or solvate thereof.

Another preferred compound of the invention is N-[3-(tert-butyl-methyl-amino)-butyl]-4-(6-fluoro-3-oxo-1,3-dihydro-pyrazolo[4,3-c]cinnolin-2-yl)-benzamide, of formula (B):

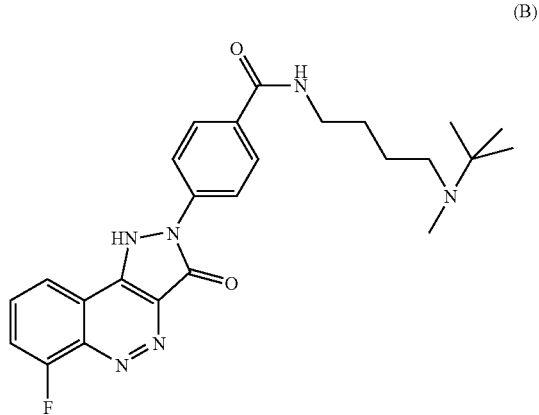

(B)

or a pharmaceutically or veterinarily acceptable salt, hydrate or solvate thereof.

As mentioned above, the invention includes pharmaceutical or veterinary composition comprising a compound of formula (I) or a pharmaceutically or veterinarily acceptable salt thereof together with a pharmaceutically or veterinarily acceptable excipient or carrier. In such compositions, it will be understood that the specific dose level for any particular patient will depend upon a variety of factors including the activity of the specific compound employed, the age, body weight, general health, sex, diet, time of administration, route of administration, rate of excretion, drug combination and the cause and severity of the particular disease undergoing therapy. Optimum dose levels and frequency of dosing will be determined by clinical trial.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzallkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Embodiments of the invention are described in the following non-limiting Examples:

The following abbreviations are used in the experimental descriptions:

| | |
|---|---|
| DMF | Dimethyl formamide |
| DMA | Dimethyl acetamide |
| DMSO | Dimethyl sulphoxide |
| HBTU | O-Benzotriazol-1-yl-N,N,N',N'-tetramethyluronium hexafluorophosphate |
| HPLC | High performance liquid chromatography |
| LCMS | Liquid chromatography mass spectrum |
| NMR | Nuclear magnetic resonance spectroscopy |

EXAMPLE 1

Step 1: Preparation of (henylhydrazono)malonic acid

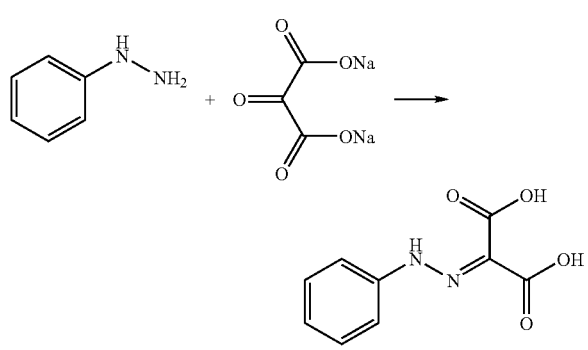

Sodium mesoxalate monohydrate (5.00 g, 27.8 mmol) was dissolved in 1 M hydrochloric acid (50 ml) to give a colourless cloudy solution. Phenylhydrazine (3.00 g, 2.72 ml, 27.8 mmol) was added dropwise at room temperature to the stirred mixture. A yellow precipitate formed, was collected by filtration after 90 min and washed with water (50 ml). The filter cake was triturated with ethyl acetate/hexane [1:1], filtered and dried under vacuum. The title compound was isolated as a yellow powder (4.74 g, 22.7 mmol, 82%). LCMS: m/z 207 [M–H]$^+$.

Alternatively the product can be extracted from the aqueous phase with ethyl acetate (2×250 ml), the organic phase dried over magnesium sulphate, filtered and the solvent removed under vacuum.

Step 2: Preparation of (phenylhydrazono)malonoyl dichloride

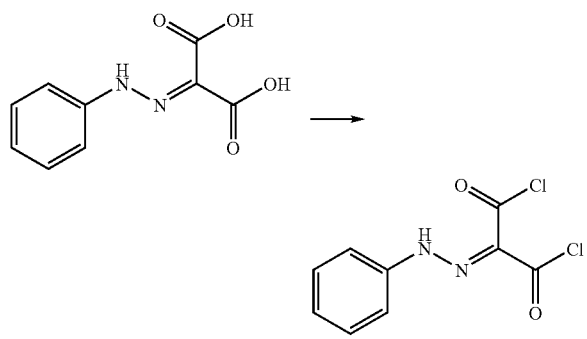

(Phenylhydrazono)malonic acid (1.00 g, 4.80 mmol) was mixed under inert atmosphere with dry chloroform (15 ml) to give a yellow suspension. The mixture was stirred at room temperature and phosphorus pentachloride (2.19 g, 10.5 mmol) was added portionwise. The reaction mixture was heated to reflux for 1.5 h to give a green solution. The mixture was cooled to room temperature and diluted with hexane (15 ml). A green precipitate formed, was collected by filtration and dried under vacuum. The title compound was isolated as a green powder (645 mg, 2.63 mmol, 53%).

Step 3: Preparation of methyl 4-hydroxycinnoline-3-carboxylate

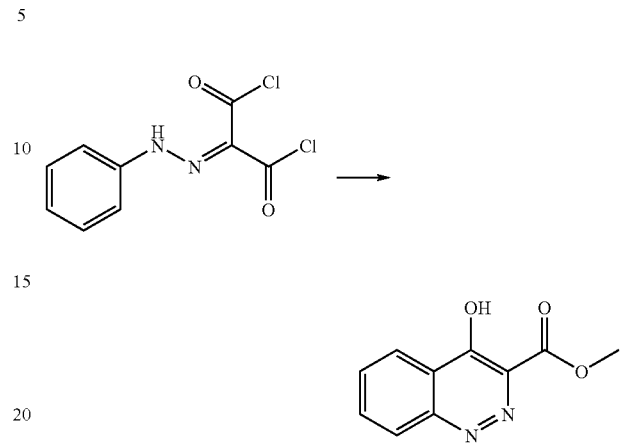

(Phenylhydrazono)malonoyl dichloride (2.45 g, 0.01 mmol) was mixed under inert atmosphere with 1,2-dichloroethane (15 ml) to give a yellow suspension. Titanium tetrachloride (1.89 g, 1.09 ml) was added dropwise to form a brown solution. The mixture was heated to reflux overnight, cooled to room temperature and quenched dropwise with methanol (15 ml). Stirring was continued for 30 min and volatiles were removed under vacuum. Water (100 ml) was added and the obtained suspension was extracted with n-butanol (2×50 ml). The combined organic phases were washed with water (2×20 ml) and concentrated under vacuum. The title compound was isolated as a green solid (1.04 g, 5.10 mmol, 51%). LCMS: m/z 205 [M+H]$^+$.

Step 4: Preparation of methyl 4-chlorocinnoline-3-carboxylate

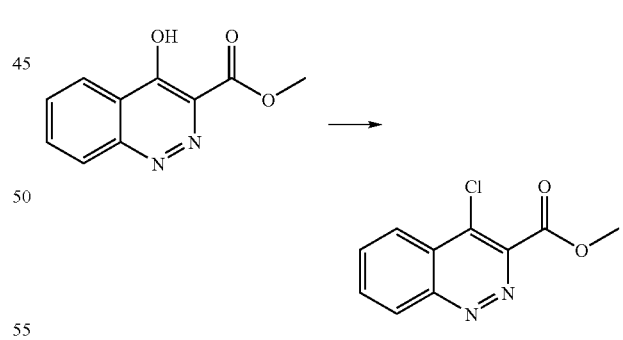

Thionyl chloride (8.15 g, 5 ml) was added dropwise under inert atmosphere to methyl 4-hydroxycinnoline-3-carboxylate (0.50 g, 2.45 mmol). The mixture was heated to reflux for 1.5 h, cooled to room temperature and excess thionyl chloride was removed under vacuum. Toluene (5 ml) was added to the residue. The mixture was stirred at room temperature overnight. The solids were collected by filtration and dried under vacuum. The title compound was isolated as a brown solid (248 mg, 1.11 mmol, 45%). LCMS: m/z 223 [M+H]$^+$.

Step 5: Preparation of 4-(3-oxo-1,3-dihydro-2H-pyrazolo[4,3-c]cinnolin-2-yl)benzoic acid

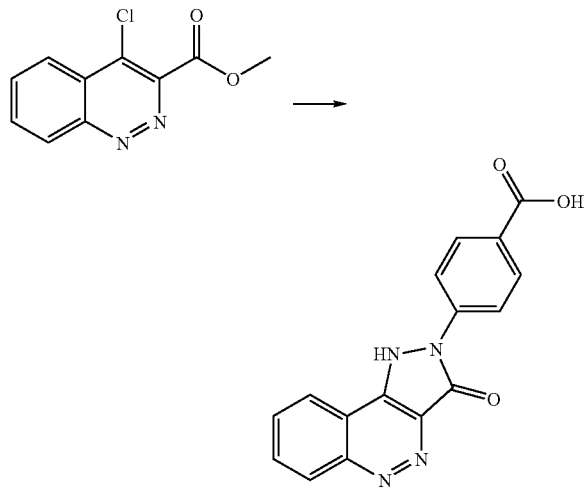

4-Hydrazinobenzoic acid (68.4 mg, 0.45 mmol) was mixed at room temperature with ethanol (5 ml) to give a creme-coloured suspension. Methyl 4-chlorocinnoline-3-carboxylate (100 mg, 0.45 mmol) was added and the mixture was heated to 45-50° C. for 1 h. The reaction mixture was cooled to room temperature and the solvent was removed under vacuum. Ethyl acetate (10 ml) was added to the residue. The mixture was stirred at room temperature for 1 h. The solids were collected by filtration and dried under vacuum. The title compound was isolated as a brown powder (120 mg, 0.39 mmol, 86%). LCMS: m/z 307 [M+H]$^+$. NMR [DMSO-d$_6$]: δ=7.69-7.77 (m, 1H$_{aryl}$); 7.81-7.90 (m, 2H$_{aryl}$); 8.05 (d, J=8.85, 2H$_{aryl}$); 8.20 (d, J=7.92 Hz, 1H$_{aryl}$); 8.33 (d, J=8.85 Hz, 2H$_{aryl}$); 14.64 (s, NH).

Alternatively the reaction may be carried out at room temperature. In this case, a longer reaction time of 2-3 h may be required.

EXAMPLE 2

Preparation of N-[(dimethylamino)propyl]-4-(3-oxo-1,3-dihydro-2H-pyrazolo[4,3-c]cinnolin-2-yl)benzamide

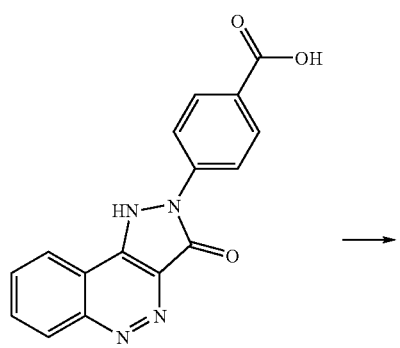

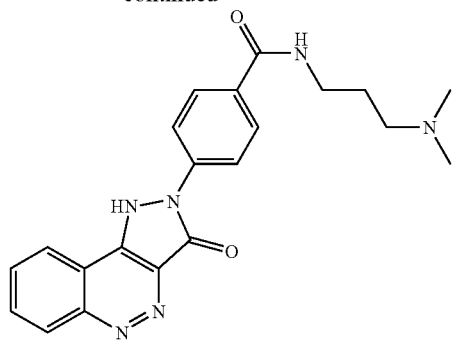

4-(3-oxo-1,3-dihydro-2H-pyrazolo[4,3-c]cinnolin-2-yl) benzoic acid (25 mg, 0.08 mmol) was mixed with DMF (1 ml). Diisopropylethylamine (21 mg, 28 μl, 0.16 mmol) and 3-dimethylaminopropylamine (8.2 mg, 10.0 μl, 0.09 mmol) were added followed by HBTU (30.3 mg, 0.08 mmol). The mixture was stirred at room temperature for 2 h. The product was purified by preparative HPLC. The title compound was isolated as a red solid (12.6 mg, 0.032 mmol, 40%). LCMS: m/z 391 [M+H]$^+$.

EXAMPLE 3

Preparation of N-benzyl-4-(3-oxo-1,3-dihydro-2H-pyrazolo[4,3-c]cinnolin-2-yl)benzamide

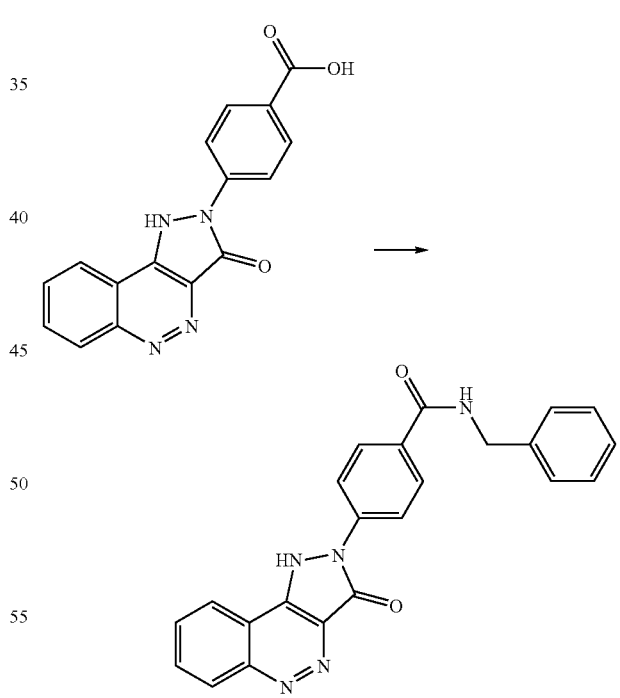

4-(3-oxo-1,3-dihydro-2H-pyrazolo[4,3-c]cinnolin-2-yl) benzoic acid (52 mg, 0.17 mmol) was mixed with DMF (2 ml). Diisopropylethylamine (22 mg, 29 μl, 0.17 mmol) and benzylamine (18.2 mg, 18.6 μl, 0.17 mmol) were added followed by HBTU (64.5 mg, 0.17 mmol). The mixture was stirred at room temperature for 4 h. The product was purified by preparative HPLC. The title compound was isolated as a red solid (6.6 mg, 0.02 mmol, 10%). LCMS: m/z 396 [M+H]$^+$.

EXAMPLE 4

Step 1: Preparation of 4-(3-oxo-1,3-dihydro-2H-pyrazolo[4,3-c]cinnolin-2-yl)benzoyl chloride

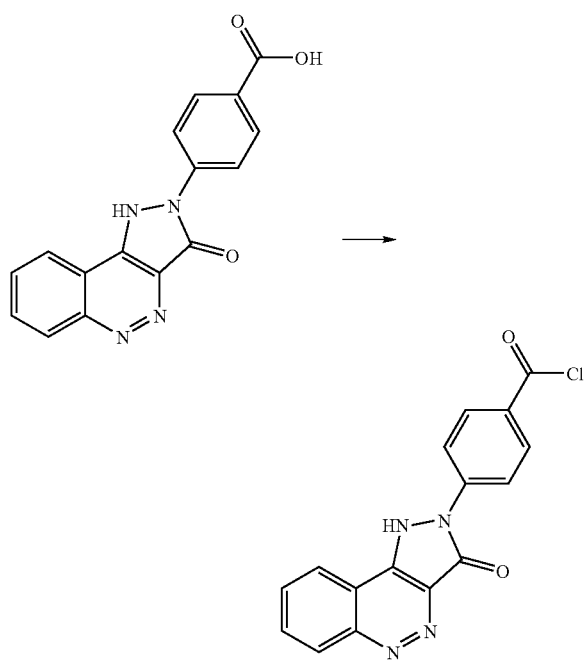

Thionyl chloride (90 ml) was added to 4-(3-oxo-1,3-dihydro-2H-pyrazolo-[4,3-c]cinnolin-2-yl)benzoic acid (2.36 g, 7.70 mmol). The mixture was heated to reflux for 2 h under nitrogen atmosphere. A dark red solution was obtained, cooled to room temperature and excess thionyl chloride was removed under vacuum. Toluene (30 ml) was added to the residues and the mixture was stirred at room temperature under nitrogen atmosphere until precipitation was complete. The solids were collected by filtration and washed with toluene (2×30 ml). The title compound was isolated as a red solid (2.20 g, 6.77 mmol, 88%) LCMS: m/z 321 [M+H]⁺ (methyl ester resulting from sample make-up in methanol).

Step 2: Preparation of N-[(cyclohexylamino)propyl]-4-(3-oxo-1,3-dihydro-2H-pyrazolo[4,3-c]cinnolin-2-yl)benzamide

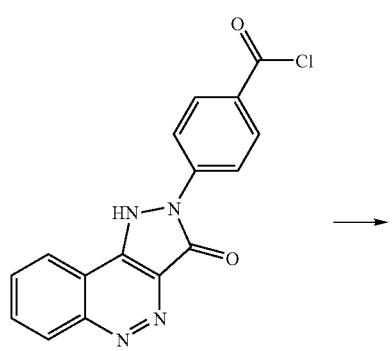

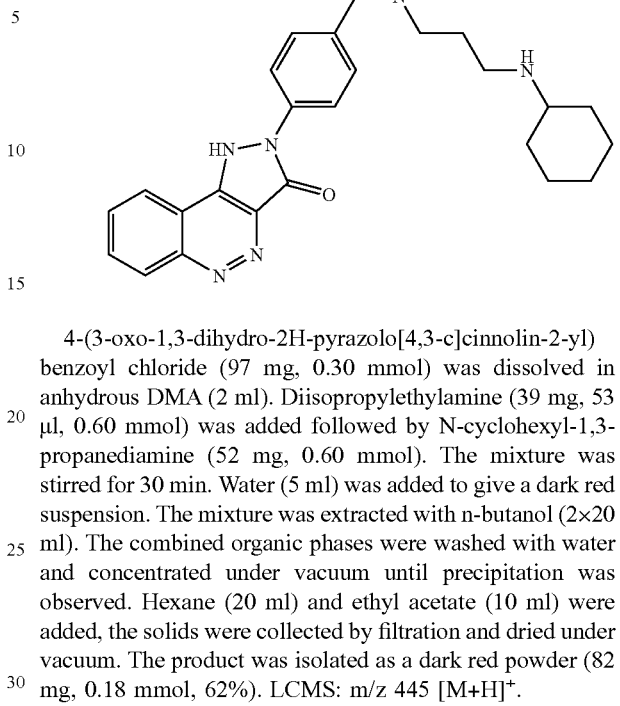

4-(3-oxo-1,3-dihydro-2H-pyrazolo[4,3-c]cinnolin-2-yl) benzoyl chloride (97 mg, 0.30 mmol) was dissolved in anhydrous DMA (2 ml). Diisopropylethylamine (39 mg, 53 µl, 0.60 mmol) was added followed by N-cyclohexyl-1,3-propanediamine (52 mg, 0.60 mmol). The mixture was stirred for 30 min. Water (5 ml) was added to give a dark red suspension. The mixture was extracted with n-butanol (2×20 ml). The combined organic phases were washed with water and concentrated under vacuum until precipitation was observed. Hexane (20 ml) and ethyl acetate (10 ml) were added, the solids were collected by filtration and dried under vacuum. The product was isolated as a dark red powder (82 mg, 0.18 mmol, 62%). LCMS: m/z 445 [M+H]⁺.

EXAMPLE 5

Step 1: Preparation of [(2-Fluorophenyl)hydrazono]malonic acid

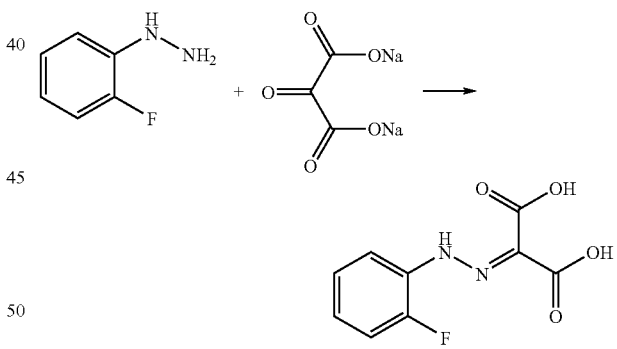

Sodium mesoxalate monohydrate (2.21 g, 12.3 mmol) was dissolved in 1 M hydrochloric acid (50 ml) to give a colourless cloudy solution. 2-Fluoro-phenylhydrazine hydrochloride (2.00 g, 12.3 mmol) was added portionwise at room temperature to the stirred mixture. A yellow precipitate formed, the mixture was diluted with water (50 ml) and stirring continued overnight. Ethyl acetate (150 ml) was added, the phases were mixed vigorously until the solids had dissolved. The phases were separated and the aqueous phase was washed with ethyl acetate (50 ml). The combined organic phases were dried over magnesium sulfate, filtered and the solvent removed under vacuum. The title compound was isolated as a yellow powder (2.55 g, 11.7 mmol, 92%). LCMS: m/z 227 [M−H]⁺.

Step 2: Preparation of
[(2-Fluorophenyl)hydrazono]malonoyl dichloride

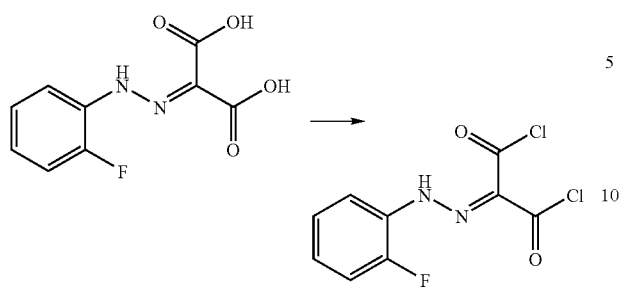

(2-Fluorophenylhydrazono)malonic acid (1.33 g, 5.88 mmol) was mixed under inert atmosphere with dry chloroform (20 ml) to give a yellow suspension. The mixture was stirred at room temperature and phosphorus pentachloride (2.69 g, 12.9 mmol) was added portionwise. The reaction mixture was heated to reflux for 2 h to give a dark yellow solution. The mixture was cooled to room temperature and concentrated under vacuum until precipitation occurred. The solids were collected by filtration, washed with hexane (30 ml) and dried under vacuum. The title compound was isolated as a yellow powder (760 mg, 2.89 mmol, 49%).

Step 3: Preparation of methyl
8-fluoro-4-hydroxycinnoline-3-carboxylate

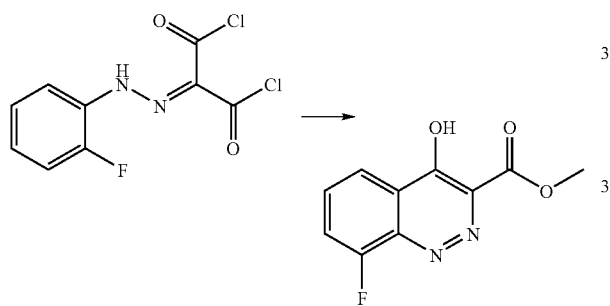

(2-Fluorophenylhydrazono)malonoyl dichloride (19.4 g, 74 mmol) was mixed under inert atmosphere with 1,2-dichloroethane (100 ml) to give a yellow suspension. Titanium tetrachloride (13.9 g, 8.08 ml, 74 mmol) was added dropwise to form a brown solution. The mixture was heated to reflux overnight. Further titanium tetrachloride (13.9 g, 8.08 ml, 74 mmol) was added and heating continued for 24 h. The reaction mixture was cooled to 0-5° C. and quenched dropwise with methanol (50 ml). Stirring was continued for 1 h at room temperature and volatiles were removed under vacuum. Water (300 ml) was added and the obtained suspension was extracted with ethyl acetate (3×100 ml). The combined organic phases were dried over magnesium sulphate, filtered and concentrated under vacuum. A yellow solid was obtained (12 g crude product). LCMS: m/z 223 [M+H]⁺.

Step 4: Preparation of 4-(6-fluoro-3-oxo-1,3-dihydro-2H-pyrazolo[4,3-c]cinnolin-2-yl)benzoic acid

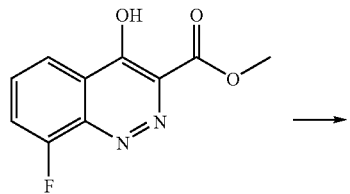

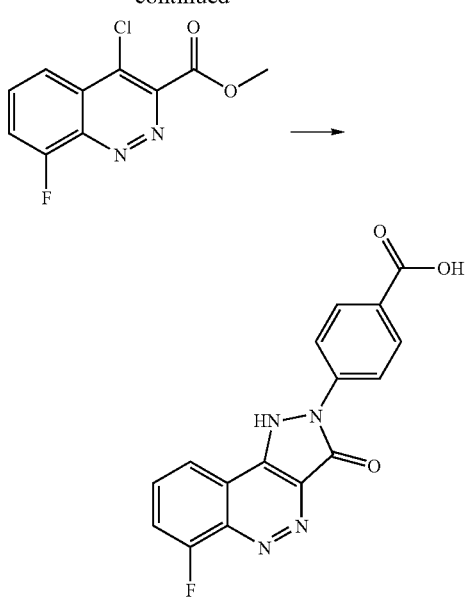

Crude 8-Fluoro-4-hydroxycinnoline-3-carboxylate from the previous stage (1.00 g, 4.95 mmol) was dissolved in thionyl chloride (50 ml). The solution was heated to reflux for 2-3 h until no further gas evolution was observed. The reaction mixture was cooled to room temperature and excess thionyl chloride was removed under vacuum. The crude intermediate was azeotroped with toluene (3×25 ml). A dark brown solid was obtained, which was taken up in ethanol (25 ml). 4-Hydrazinobenzoic acid (640 mg, 4.21 mmol) was added and the mixture was stirred at room temperature overnight. The solids were collected by filtration, slurried in 1 M HCl (100 ml), filtered, washed with hexane (50 ml) and dried under vacuum. A brown solid was obtained (890 mg of crude product). LCMS: m/z [M+H]⁺ 325.

EXAMPLE 6

Step 1: Preparation of 4-(6-fluoro-3-oxo-1,3-dihydro-2H-pyrazolo[4,3-c]cinnolin-2-yl)benzoic acid chloride

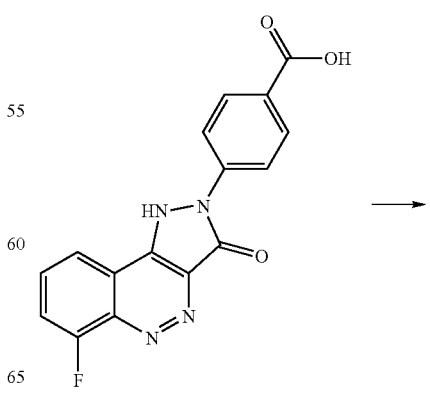

-continued

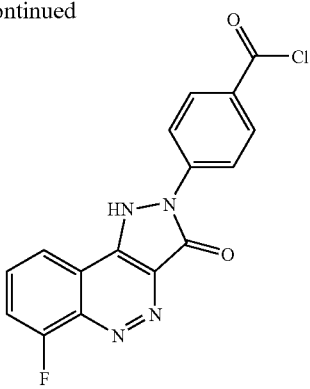

Crude 4-(6-fluoro-3-oxo-1,3-dihydro-2H-pyrazolo[4,3-c]cinnolin-2-yl)-benzoic acid (1.45 g) from the previous stage was dissolved in thionyl chloride (50 ml). The mixture was heated to 70° C. for 2-3 h until no further gas evolution was observed. The mixture was cooled to room temperature and excess thionyl chloride was removed under vacuum. The residues were azeotroped with toluene (2×20 ml) to give a solid. The solid was collected by filtration, washed with toluene and dried under vacuum. The product was isolated as a yellow powder (670 mg, 1.95 mmol). LCMS: m/z [M+H]$^+$ 339 (methyl ester resulting from sample make-up in methanol).

Step 2: Preparation of 4-(6-fluoro-3-oxo-1,3-dihydro-2H-pyrazolo[4,3-c]cinnolin-2-yl)-N-(pyrrolidin-1-yl-butyl)benzamide

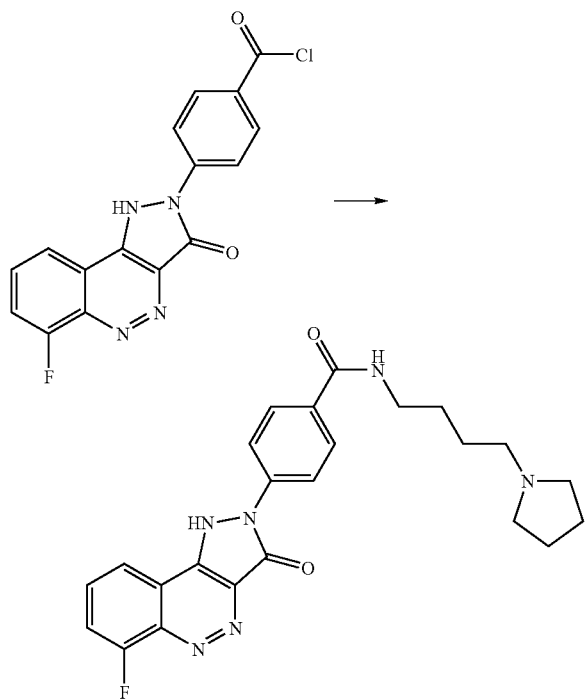

4-(6-fluoro-3-oxo-1,3-dihydro-2H-pyrazolo[4,3-c]cinnolin-2-yl)benzoyl chloride (100 mg, 0.29 mmol) was dissolved in anhydrous DMA (2 ml). Diisopropylethylamine (75 mg, 101 µl, 0.58 mmol) was added followed by 1-(4-aminobutyl)pyrrolidine (41 mg). The mixture was stirred at room temperature overnight. Water (5 ml) and n-butanol (5 ml) were added. The phases were separated. The organic phase was washed with water (2×5 ml). The volatiles were removed under vacuum. The product was isolated as a brown powder (50 mg, 0.11 mmol, 37%). LCMS: m/z [M+H]$^+$ 463.

EXAMPLE 7

Preparation of 4-(6-fluoro-3-oxo-1,3-dihydro-2H-pyrazolo[4,3-c]cinnolin-2-yl)-N-(1,2,2,6,6-pentamethylpiperidine-4-yl)benzamide

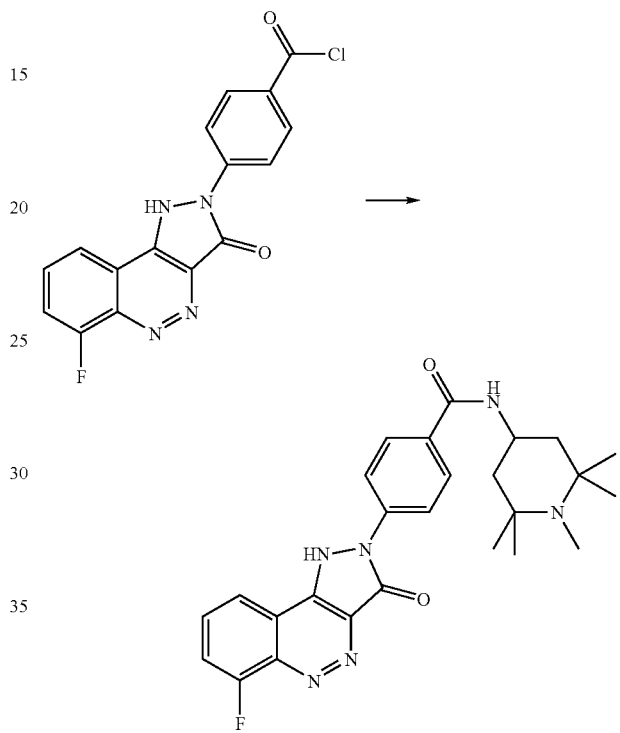

4-(6-fluoro-3-oxo-1,3-dihydro-2H-pyrazolo[4,3-c]cinnolin-2-yl)benzoyl chloride (100 mg, 0.29 mmol) was dissolved in anhydrous DMA (2 ml). Diisopropylethylamine (75 mg, 101 µl, 0.58 mmol) was added followed by 4-amino-1,2,2,6,6-pentamethylpiperidine (49 mg, 0.29 mmol). The mixture was stirred overnight. Water (5 ml) and n-butanol (5 ml) were added. The phases were separated. The organic phase was washed with water (2×5 ml) and the solution was concentrated under vacuum. The title compound was isolated as a dark red solid (50 mg, 0.105 mmol, 36%). LCMS: m/z [M+H]$^+$ 477.

EXAMPLE 8

Step 1: Preparation of 2-(4-nitrophenyl)-1,2-dihydro-3H-pyrazolo[4,3-c]cinnolin-3-one

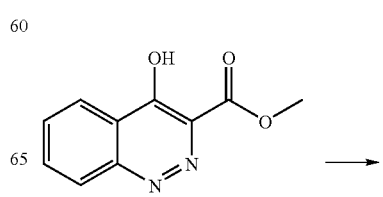

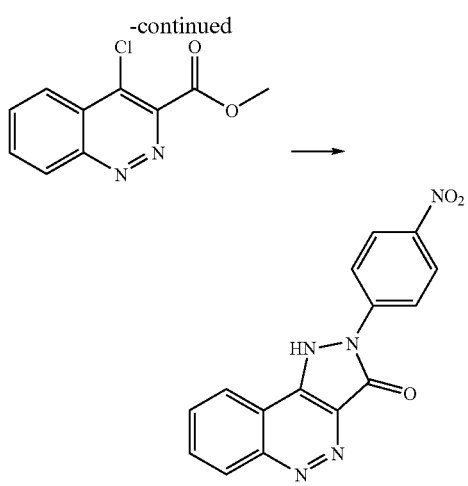

Thionyl chloride (326 g, 200 ml) was added dropwise under inert atmosphere to methyl 4-hydroxycinnoline-3-carboxylate (10.0 g, 49 mmol). The mixture was heated to reflux for 2.5 h, cooled to room temperature and excess thionyl chloride was removed under vacuum. Toluene (100 ml) was added to the residue and removed under vacuum. This procedure was repeated with further toluene (100 ml). A brown semi-solid material was obtained and taken up in ethanol (200 ml). 4-Nitrophenylhydrazine (5.99 g, 39.2 mmol) was added portionwise. The mixture was stirred at room temperature overnight. The mixture was heated to 40-45° C. for 1 h and cooled to room temperature. The solids were collected by filtration, triturated with ethanol (100 ml) and dried under vacuum. The title compound was isolated as a brown solid (8.42 g, 27.4 mmol, 70%). LCMS: m/z 308 [M+H]$^+$.

Step 2: Preparation of 2-(4-aminophenyl)-1,2-dihydro-3H-pyrazolo[4,3-c]cinnolin-3-one

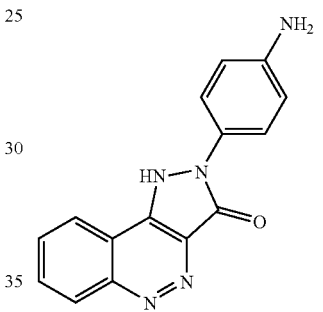

2-(4-nitrophenyl)-1,2-dihydro-3H-pyrazolo[4,3-c]cinnolin-3-one (11.4 g, 37.2 mmol) was suspended in a mixture of ethanol (100 ml) and water (100 ml). Iron powder (11.1 g, 200 mmol) and ammonium chloride (5.34 g, 100 mmol) were added. The mixture was heated to 80° C. overnight, cooled to room temperature and basified with potassium carbonate to pH 9-10. The solids were removed by filtration through a pad of Celite®. The filtrate was extracted with n-butanol (2×200 ml). The combined organic phases were concentrated under vacuum to give a dark red solid. The solid was triturated with methanol (100 ml), filtered and dried under vacuum. The title compound was isolated as a dark red powder (5.58 g, 20.1 mmol, 57%). LCMS: m/z 278 [M+H]$^+$.

Step 3: Preparation of N-[3-(dimethylamino)propyl]-N'-[4-(3-oxo-1,3-dihydro-2H-pyrazolo[4,3-c] cinnolin-2-yl) phenyl]urea

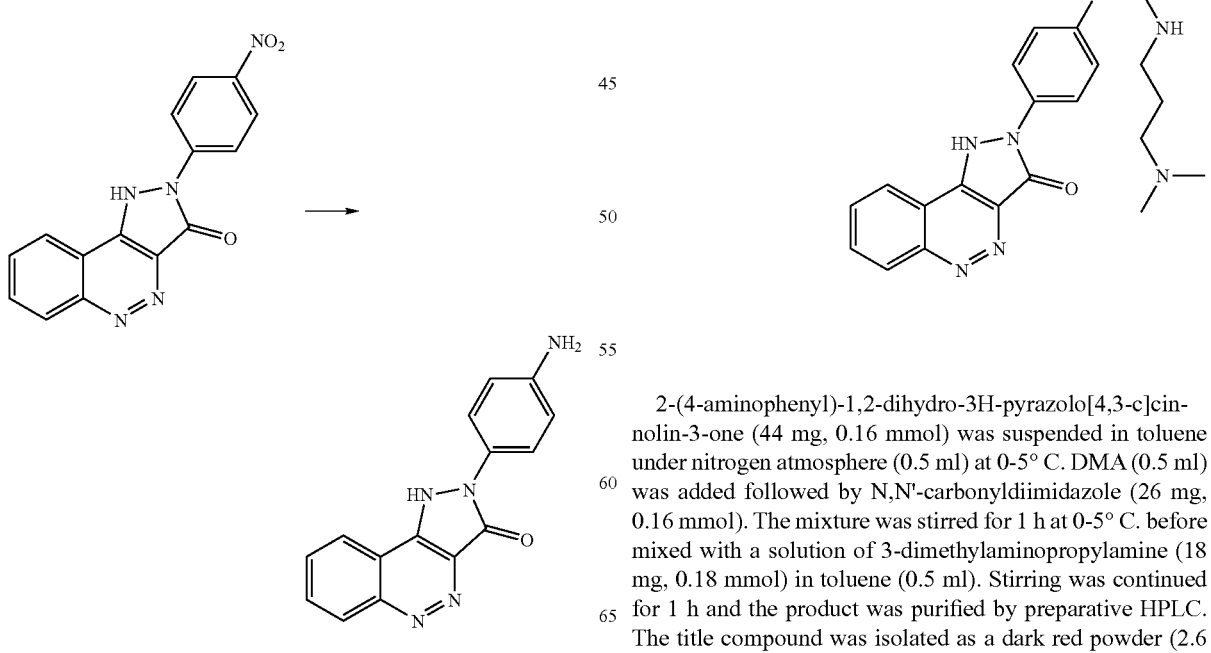

2-(4-aminophenyl)-1,2-dihydro-3H-pyrazolo[4,3-c]cinnolin-3-one (44 mg, 0.16 mmol) was suspended in toluene under nitrogen atmosphere (0.5 ml) at 0-5° C. DMA (0.5 ml) was added followed by N,N'-carbonyldiimidazole (26 mg, 0.16 mmol). The mixture was stirred for 1 h at 0-5° C. before mixed with a solution of 3-dimethylaminopropylamine (18 mg, 0.18 mmol) in toluene (0.5 ml). Stirring was continued for 1 h and the product was purified by preparative HPLC. The title compound was isolated as a dark red powder (2.6 mg, 6 μmol, 4%). LCMS: m/z 406 [M+H]$^+$.

EXAMPLE 9

Preparation of 4-(3-oxo-1,3-dihydro-2H-pyrazolo[4,3-c]cinnolin-2-yl)benzoic acid ethyl ester.

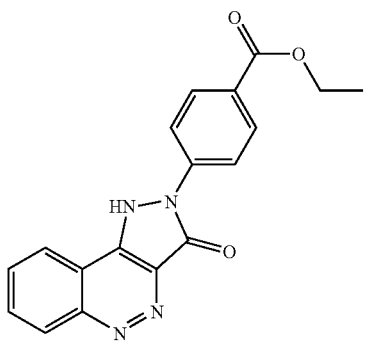

The title compound was prepared by the method of Example 1 step 5, substituting 4-hydrazinobenzoic acid ethyl ester for the parent acid. MS: MH+=335.2

Results

The use of BIAcore Biomolecular Interaction Analysis

Biotinylated human CD80 (hCD80-BT) is a recombinant soluble form of a membrane bound receptor molecule (CD80) which binds to CD28 to initiate T cell activation. The interaction between CD80 and CD28 has been extensively investigated (Collins et al, 2002). Biotinlyated human HLA-A2-tax is the recombinant soluble form of a membrane bound receptor molecule that has been used in this example as a control protein, and is not expected to interact with the compounds.

The BIAcore S51™ system was used for screening the compounds of Examples 1-4 above. A series S sensor chip CM5 was docked onto the BIAcore S51™. Streptavidin was coupled to the carboxymethyl surface using standard amine coupling. The chip surface was activated with 0.2M EDC/0.05M NHS, followed by binding of streptavidin (0.25 mg/ml in 10 mM sodium acetate pH 5.0) and saturation of unoccupied sites with 1 M ethylenediamine.

The BIAcore S51 sensor chip has two separate sensor spots for immobilisation of proteins. hCD80-BT was immobilised on the streptavidin-coated surface of one sensor spot until a response of approximately 3000 RU was observed. A protein to control for non-specific binding of the compound was immobilised on a second sensor spot. The control protein used for these experiments was a biotinylated, soluble form of the human HLA protein.

Dilution series of compounds (1000 nM-0.05 nM) were prepared in running buffer (10 mM, pH 7.4, 150 mM NaCl, 0.005% P20; 5% DMSO).

BIAcore S51™ was run at a flow rate of 30 µl/min using running buffer. Compounds and DMSO standard solutions for correction of data for solvent effects were injected. Data were recorded automatically and were analysed using BIAcore S51 Evaluation software.

The interaction between CD80 and the endogenous protein ligand (CD28) is highly specific, but relatively weak, with a $K_D$ of 4750 nM, and an off-rate of greater than 0.2 s$^{-1}$. The compounds of Examples 2,3,4,6,7 have greater affinity and longer residence times on CD80 than CD28, having $K_D$S of less than 100 nM, and off-rates of $2 \times 10^{-2}$, indicating that the cinnolines will be able to compete effectively with the endogenous ligand. The cinnolines showed no detectable interaction with the control protein.

REFERENCES

Collins AV et al. (2002) Immunity 17, 201-210 "The interaction properties of costimulatory molecules revisited"

Inhibition of Production of Interleukin-2 (IL-2) by Human Jurkat T Cells.

Method

Human Raji cells were dispensed at a concentration of $2 \times 10^5$ cells per well in RPMI-1640 medium supplemented with 10% fetal calf serum, 1% penicillin/streptomycin, 1% glutamine (RPMI medium) in a 96-well round bottom microtitre plate. Compounds under investigation (dissolved in 100% DMSO) were diluted to eight-fold the desired final concentration in RPMI medium and added to the required final concentration for a total volume of 200 µl per well. After 20 minutes incubation at 37° C., Jurkat T cells were added at a concentration of $2 \times 10^5$ cells per well. Monoclonal antibody to CD3 (UCHT1, R&D Systems) was added to the cultures at a final concentration of 1 µg per ml, and where indicated, monoclonal antibody to CD28 (CD28.2, BD-Pharmingen) was also added at a concentration of 2.5 µg per ml. Cells were cultured at 37° C. for 5 hours, after which the plates were centrifuged and the supernatants harvested for IL-2 ELISA assay using the IL-2 Eli-pair kit (DIACLONE Research, Besancon, France) according to the manufacturers instructions.

By way of example, the compound of Example 2 (AV1142005) gave 65% inhibition at 30 µM.

Homogenous Time Resolved Fluorescence Assay

The examples described above were tested in a cell free Homogenous Time Resolved Fluorescence (HTRF) assay to determine their activity as inhibitors of the CD80-CD28 interaction.

In the assay, europium and allophycocyanin (APC) are associated with CD28 and CD80 indirectly (through antibody linkers) to form a complex, which brings the europium and APC into close proximity to generate a signal. The complex comprises the following six proteins: fluorescent label 1, linker antibody 1, CD28 fusion protein, CD80 fusion protein, linker antibody 2, and fluorescent label 2. The table below describes these reagents in greater detail.

| | |
|---|---|
| Fluorescent label 1 | Anti-Rabbit IgG labelled with Europium (1 µg/ml) |
| Linker antibody 1 | Rabbit IgG specific for mouse Fc fragment (3 µg/ml) |
| CD28 fusion protein | CD28 - mouse Fc fragment fusion protein (0.48 µg/ml) |
| CD80 fusion protein | CD80 mouse Fab fragment (C215) fusion protein (1.9 µg/ml) |
| Linker antibody 2 | GαMκ-biotin: biotinylated goat IgG specific for mouse kappa chain (2 µg/ml) |
| Fluorescent label 2 | SA-APC: streptavidin labelled allophycocyanin (8 µg/ml) |

On formation of the complex, europium and APC are brought into proximity and a signal is generated.

Non-specific interaction was measured by substituting a mouse Fab fragment (C215) for the CD80 mouse Fab fragment fusion protein (1.9 µg/ml). The assay was carried out in black 384 well plates in a final volume of 30 µl. Assay buffer: 50 mM Tris-HCl, 150 mM NaCl pH7.8, containing 0.1% BSA (w/v) added just prior to use.

Compounds were added to the above reagents in a concentration series ranging between 100 µM-1.7 nM. The reaction was incubated for 4 hours at room temperature. Dual measurements were made using a Wallac Victor 1420 Multilabel Counter. First measurement: excitation 340 nm, emission 665 nm, delay 50 µs, window time 200 µs. second measurement: excitation 340 nm, emission 615 nm, delay 50 µs, window time 200 µs. Counts were automatically corrected for fluorescence crossover, quenching and background. The EC50 activities of compounds tested are recorded as:

EC50: *=>10 µM,*=1-10 µM,=<1 µM.

The compounds of Examples 1-8 had the following activities in the HTRF assay described above:
EXAMPLE 1*
EXAMPLE 2***
EXAMPLE 3***
EXAMPLE 4***
EXAMPLE 5*
EXAMPLE 6***
EXAMPLE 7***
EXAMPLE 8***
EXAMPLE 9**

Additional Examples

Further examples of compounds of the invention were synthesised by methods analogous to those of Examples 1-8 above. The structures of the synthesised compounds are shown in the following Table, together with their activities in the HTRF assay described above.

TABLE

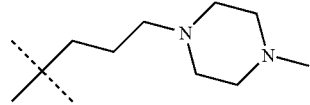

| Example No. | X | W | R | R' | MS MH+ | Activity |
|---|---|---|---|---|---|---|
| 9a. | H | — | CH$_2$CH$_2$OMe | H | 364.2 | ** |
| 10. | H | — | 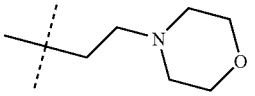 | H | 446.2 | *** |
| 11. | H | — | CH$_2$CH$_2$NMe$_2$ | H | 377.1 | *** |
| 12. | H | — | 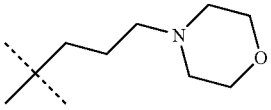 | H | 419.1 | *** |
| 13. | H | — | 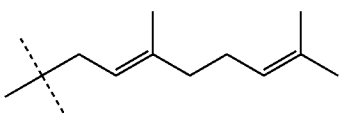 | H | 433.1 | *** |
| 14. | H | — | | H | 442.0 | * |
| 15. | H | — | Ph | H | 382.0 | ** |

TABLE-continued
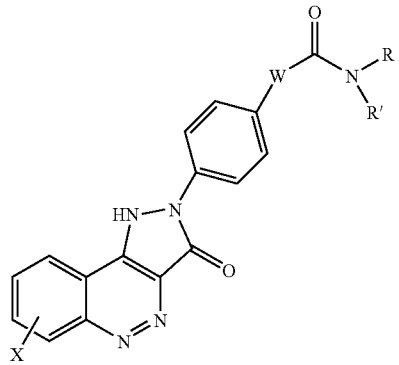
| Example No. | X | W | R | R' | MS MH+ | Activity |
|---|---|---|---|---|---|---|
| 16. | H | — | 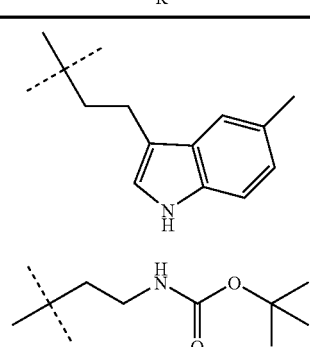 | H | 463.0 | * |
| 17. | H | — | 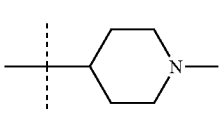 | H | 448.8 | ** |
| 18. | H | — | 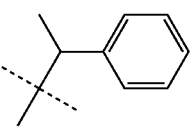 | H | 403.1 | *** |
| 19. | H | — | 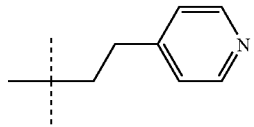 | H | 410.0 | * |
| 20. | H | — | 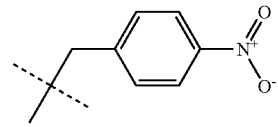 | H | 411.0 | *** |
| 21. | H | — | 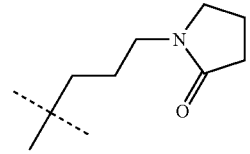 | H | 441.2 | ** |
| 22. | H | — | 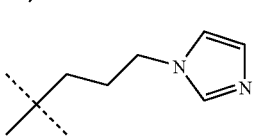 | H | 431.1 | ** |
| 23. | H | — |  | H | 414.1 | *** |

TABLE-continued
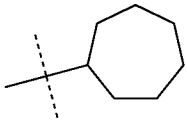
| Example No. | X | W | R | R' | MS MH+ | Activity |
|---|---|---|---|---|---|---|
| 24. | H | — | 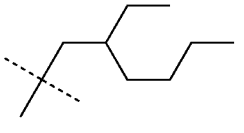 | H | 402.2 | ** |
| 25. | H | — | 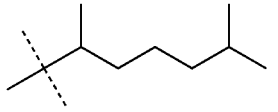 | H | 418.4 | * |
| 26. | H | — | 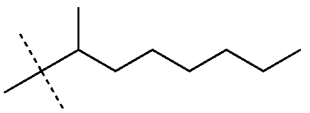 | H | 418.2 | *** |
| 27. | H | — | 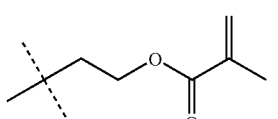 | H | 418.2 | * |
| 28. | H | — | 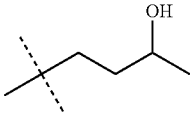 | H | 417.9 | ** |
| 29. | H | — | 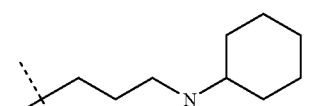 | H | 378.0 | *** |
| 30. | H | — | 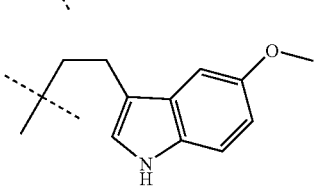 | H | 445.2 | *** |
| 31. | H | — |  | H | 479.0 | ** |

TABLE-continued

| Example No. | X | W | R | R' | MS MH+ | Activity |
|---|---|---|---|---|---|---|
| 32. | H | — | (3-(2-methylpiperidin-1-yl)propyl) | H | 445.2 | *** |
| 33. | H | — | (2,3-dimethylbutyl) | H | 376.2 | ** |
| 34. | H | — | (ethyl 3-methylbutanoate) | H | 420.0 | ** |
| 35. | H | — | (2-(1H-imidazol-4-yl)ethyl) | H | 400.0 | ** |
| 36. | H | — | (2-(2-oxoimidazolidin-1-yl)ethyl) | H | 418.0 | * |
| 37. | H | — | (3-(4-benzylpiperazin-1-yl)propyl) | H | 508.1 | *** |
| 38. | H | — | (4-tert-butylcyclohexyl) | H | 444.2 | * |
| 39. | H | — | (3-nitrobenzyl) | H | 441.1 | ** |
| 40. | H | — | (4-morpholinophenyl) | H | 467.2 | ** |

TABLE-continued
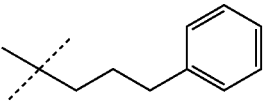
| Example No. | X | W | R | R' | MS MH+ | Activity |
|---|---|---|---|---|---|---|
| 41. | H | — | 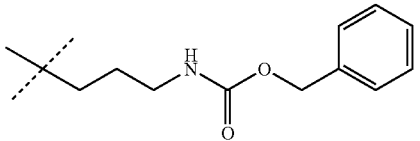 | H | 424.1 | ** |
| 42. | H | — | 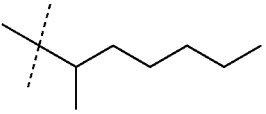 | H | 496.9 | ** |
| 43. | H | — | 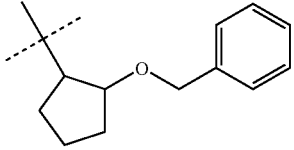 | H | 404.1 | ** |
| 44. | H | — | 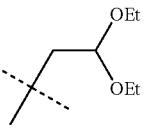 | H | 480.0 | * |
| 45. | H | — | 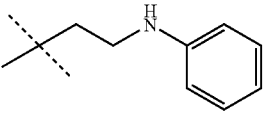 | H | 421.8 | ** |
| 46. | H | — | Et | H | 334.2 | *** |
| 47. | H | — | 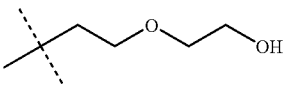 | H | 425.0 | *** |
| 48. | H | — | $CH_2CH_2NHMe$ | H | 363.0 | *** |
| 49. | H | — | $CH_2CH_2NHEt$ | H | 377.1 | *** |
| 50. | H | — |  | H | 394.2 | ** |
| 51. | H | — | $CH_2CH_2OH$ | H | 350.2 | *** |
| 52. | H | — | $CH_2CH_2CH_2NHMe$ | H | 377.2 | *** |
| 53. | H | — | $CH_2CH_2CH_2OiPr$ | H | 406.2 | *** |
| 54. | H | — | $CH_2CH_2CH_2CH_2NH_2$ | H | 377.2 | *** |

TABLE-continued

| Example No. | X | W | R | R' | MS MH+ | Activity |
|---|---|---|---|---|---|---|
| 55. | H | — | (3,5-dimethylhexyl sketch) | H | 390.2 | *** |
| 56. | H | — | (4-fluorobenzyl sketch) | H | 414.1 | ** |
| 57. | H | — | (cyclohexylmethyl sketch) | H | 388.2 | ** |
| 58. | H | — | CH$_2$CH$_2$CH$_2$N(nBu)$_2$ | H | 475.2 | *** |
| 59. | H | — | cyclododecyl | H | 472.2 | * |
| 60. | H | — | CH$_2$CH$_2$NEt$_2$ | H | 405.1 | *** |
| 61. | H | — | (3-(1-methylpyrrolidin-2-yl)propyl sketch) | H | 417.2 | *** |
| 62. | H | — | (4-methylcyclohexylmethyl sketch) | H | 402.2 | ** |
| 63. | H | — | CH$_2$CH$_2$OPh | H | 426.0 | ** |
| 64. | H | — | (4-trifluoromethoxybenzyl sketch) | H | 480.2 | ** |
| 65. | H | — | (3-(naphthalen-1-ylamino)propyl sketch) | H | 475.2 | ** |

TABLE-continued

| Example No. | X | W | R | R' | MS MH+ | Activity |
|---|---|---|---|---|---|---|
| 66. | H | — | *isobutyl-CH(CH3)-C(O)OEt group* | H | 406.1 | ** |
| 67. | H | — | CH2CH2CH2OnBu | H | 420.0 | *** |
| 68. | H | — | *2,2,6,6-tetramethyl-1-methylpiperidin-4-yl* | H | 459.3 | *** |
| 69. | H | — | *(1-ethylpyrrolidin-2-yl)methyl* | H | 417.3 | *** |
| 70. | H | — | *sec-pentyl (R isomer)* | H | 362.3 | *** |
| 71. | H | — | *sec-pentyl (S isomer)* | H | 362.3 | *** |
| 72. | H | — | CH(Et)2 | H | 376.3 | ** |
| 73. | H | — | CH2CH2CH2CH2Ph | H | 438.4 | ** |
| 74. | H | — | *CH with CH2CH2CO2Et and CO2Et* | H | 492.2 | ** |
| 75. | H | — | *1-cyclohexylethyl, gem-dimethyl* | H | 416.3 | ** |

TABLE-continued

| Example No. | X | W | R | R' | MS MH+ | Activity |
|---|---|---|---|---|---|---|
| 76. | H | — | (CH2CH2-2-pyridyl group) | H | 411.2 | ** |
| 77. | H | — | CH2CH2SEt | H | 394.2 | *** |
| 78. | H | — | Cyclopropyl | H | 346.2 | ** |
| 79. | H | — | (CH2CH2CH2-pyrrolidinyl) | H | 417.3 | *** |
| 80. | H | — | (3-(N-benzyl)piperidinyl) | H | 479.3 | *** |
| 81. | H | — | (CH(CH3)CH2CH2CH2NEt2) | H | 447.2 | *** |
| 82. | H | — | CH2CH2CH(CH3)CH3 | H | 376.2 | ** |
| 83. | H | — | cyclopentyl | H | 374.2 | ** |
| 84. | H | — | nPropyl | H | 348.2 | ** |
| 85. | H | — | CH2CH2tBu | H | 390.3 | ** |
| 86. | H | — | (4-(N-benzyl)piperidinyl) | H | 479.3 | *** |
| 87. | H | — | CH2cycloheptyl | H | 416.4 | * |
| 88. | H | — | (C(CH3)2C(CH3)3) | H | 390.3 | ** |
| 89. | H | — | (CH(CH3)CH(CH3)2) | H | 376.3 | *** |

TABLE-continued

[Structure diagram showing a pyrazolo-cinnoline core with substituents X, W, and a phenyl-C(O)-N(R)(R') group]

| Example No. | X | W | R | R' | MS MH+ | Activity |
|---|---|---|---|---|---|---|
| 90. | H | — | (1-methyl-1-(2-(benzyloxy)cyclopentyl)) | H | 480.2 | ** |
| 91. | H | — | (neopentyl-CH2CH2-NHBoc) | H | 477.1 | *** |
| 92. | H | — | (2-methyloctyl, tert-attached) | H | 432.4 | * |
| 93. | H | — | (tert-butyl-CH(iPr)-C(O)OMe) | H | 420.1 | ** |
| 94. | H | — | (1-benzyl-3-pyrrolidinyl, gem-dimethyl) | H | 465.3 | *** |
| 95. | H | — | (gem-dimethyl-CH2CH2-pyridin-3-yl) | H | 411.4 | *** |
| 96. | H | — | (2,5-dimethylhexyl branched) | H | 404.3 | ** |
| 97. | H | — | (gem-dimethyl-CH2CH2-N(Me)Boc) | H | 463.0 | ** |

TABLE-continued

| Example No. | X | W | R | R' | MS MH+ | Activity |
|---|---|---|---|---|---|---|
| 98. | H | — | 4-(piperidin-1-yl)phenyl | H | 465.4 | ** |
| 99. | H | — | 6-hydroxy-2,6-dimethylheptan-2-yl (branched) | H | 434.4 | ** |
| 100. | H | — | 3-fluorophenyl | H | 400.3 | * |
| 101. | H | — | 3-(4-Boc-piperazin-1-yl)propyl (gem-dimethyl) | H | 518.4 | *** |
| 102. | H | — | 3-(piperazin-1-yl)propyl (gem-dimethyl) | H | 418.4 | ** |
| 103. | H | — | 2,2,6,6-tetramethylpiperidin-4-yl | H | 445.4 | *** |
| 104. | H | — | 1-(ethoxycarbonyl)piperidin-4-yl | H | 461.4 | ** |
| 105. | H | — | 4-phenylbutan-2-yl (gem-dimethyl) | H | 438.4 | * |

TABLE-continued
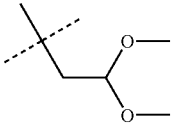
| Example No. | X | W | R | R' | MS MH+ | Activity |
|---|---|---|---|---|---|---|
| 106. | H | — | 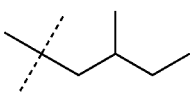 | H | 394.3 | ** |
| 107. | H | — | 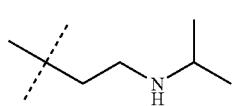 | H | 376.3 | ** |
| 108. | H | — | 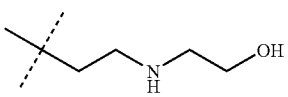 | H | 391.4 | *** |
| 109. | H | — | 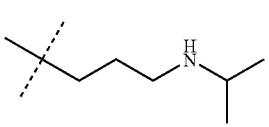 | H | 393.4 | *** |
| 110. | H | — | 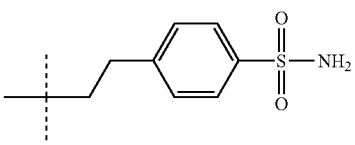 | H | 405.5 | *** |
| 111. | H | — | $CH_2CH_2CH_2OH$ | H | 364.4 | ** |
| 112. | H | — | $CH_2CH_2CH_2CH_2CH_2OH$ | H | 392.4 | *** |
| 113. | H | — | nHexyl | H | 390.4 | ** |
| 114. | H | — | 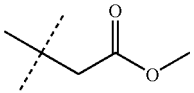 | H | 489.4 | ** |
| 115. | H | — | 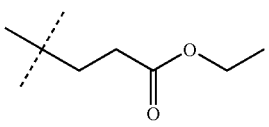 | H | 378.4 | ** |
| 116. | H | — |  | H | 406.4 | * |

TABLE-continued

| Example No. | X | W | R | R' | MS MH+ | Activity |
|---|---|---|---|---|---|---|
| 117. | H | — | (tert-butyl carbamate-hexyl chain) | H | 505.5 | ** |
| 118. | H | — | (ethyl 2-methylpropanoate) | H | 406.4 | ** |
| 119. | H | — | (2-methyl-3-methoxypropyl) | H | 378.4 | ** |
| 120. | H | — | (2-cyclohexylpropyl) | H | 416.4 | ** |
| 121. | H | — | (pinanyl group) | H | 442.4 | ** |
| 122. | H | — | (bornyl group) | H | 442.4 | * |
| 123. | H | NH | (1-benzyl-4-piperidinyl, methyl) | H | 494.3 | ** |
| 124. | H | NH | (2,4-dimethylpentyl) | H | 405.3 | * |

TABLE-continued

| Example No. | X | W | R | R' | MS MH+ | Activity |
|---|---|---|---|---|---|---|
| 125. | H | NH | CH₂CH₂-piperidinyl (gem-dimethyl) | H | 432.3 | ** |
| 126. | H | NH | CH₂-(4-fluorophenyl) (gem-dimethyl) | H | 429.3 | * |
| 127. | H | NH | cyclohexyl (gem-dimethyl) | H | 403.3 | * |
| 128. | H | NH | CH₂CH₂CH₂OEt | H | 407.2 | ** |
| 129. | H | NH | CH₂CH₂CH₂-(4-methylpiperazinyl) (gem-dimethyl) | H | 461.3 | *** |
| 130. | H | NH | CH₂CH₂NMe₂ | H | 392.2 | *** |
| 131. | H | NH | allyl | H | 361.3 | *** |
| 132. | H | NH | CH₂CH₂-morpholinyl (gem-dimethyl) | H | 434.3 | *** |
| 133. | H | NH | CH₂CH₂CH₂OMe | H | 393.2 | ** |
| 134. | H | NH | CH₂CH₂CH₂-NH-cyclohexyl (gem-dimethyl) | H | 460.3 | *** |
| 135. | H | NH | 1,2,2,6,6-pentamethylpiperidin-4-yl | H | 474.3 | ** |

TABLE-continued

| Example No. | X | W | R | R' | MS MH+ | Activity |
|---|---|---|---|---|---|---|
| 136. | H | NH | (ethyl ester group, branched) | H | 420.1 | * |
| 137. | H | NH | (branched alkyl with OH) | H | 449.2 | ** |
| 138. | H | NH | (isobutyl branched) | H | 377.3 | ** |
| 139. | H | NH | iPr | H | 363.3 | ** |
| 140. | H | NH | CH$_2$CH$_2$OMe | H | 379.3 | ** |
| 141. | H | NH | CH$_2$CH$_2$NHiPr | H | 406.2 | *** |
| 142. | H | NH | CH$_2$CH$_2$NHMe | H | 378.2 | *** |
| 143. | H | NH | CH$_2$CH$_2$NHEt | H | 392.2 | *** |
| 144. | H | NH | CH$_2$CH$_2$NHnPr | H | 406.2 | *** |
| 145. | H | NH | CH$_2$CH$_2$OCH$_2$CH$_2$OH | H | 409.2 | *** |
| 146. | H | NH | CH$_2$CH$_2$OH | H | 365.2 | *** |
| 147. | H | NH | CH$_2$CH$_2$Ph | H | 425.3 | ** |
| 148. | H | NH | CH$_2$CH$_2$CH$_2$NHiPr | H | 420.2 | *** |
| 149. | H | NH | CH$_2$CH$_2$CH$_2$OiPr | H | 421.2 | ** |
| 150. | H | NH | CH$_2$CH$_2$CH$_2$OH | H | 379.2 | *** |
| 151. | H | NH | CH$_2$CH$_2$CH$_2$CH$_2$CH$_2$OH | H | 407.2 | ** |
| 152. | H | NH | (naphthylaminoethyl) | H | 490.1 | * |
| 153. | H | NH | (tetrahydrofuranone) | H | 405.3 | ** |
| 154. | H | NH | (methyl ester branched) | H | 393.1 | ** |

TABLE-continued

| Example No. | X | W | R | R' | MS MH+ | Activity |
|---|---|---|---|---|---|---|
| 155. | H | NH | (CH₂)₂-C₆H₄-NO₂ group | H | 470.3 | ** |
| 156. | H | NH | CH₂CH₂C(O)OEt group | H | 421.2 | ** |
| 157. | H | NH | CH₂C(O)NH₂ group | H | 378.1 | ** |
| 158. | H | NH | CH(CH₃)C(O)OEt group | H | 421.1 | ** |
| 159. | H | NH | CH₂CH₂CH₂OC₁₂H₂₅ | H | 547.3 | *** |
| 160. | H | NH | CH₂CH₂CH₂OnBu | H | 435.2 | * |
| 161. | H | NH | CH₂CH₂CH₂SMe | H | 409.2 | ** |
| 162. | H | NH | CH₂-(N-ethylpyrrolidin-2-yl) group | H | 432.3 | *** |
| 163. | H | NH | (CH₂)₆NHC(O)OtBu group | H | 519.9 | ** |
| 164. | H | NH | 2-(ethoxycarbonyl)cyclopentyl group | H | 461.2 | * |
| 165. | H | NH | CH₂C(CH₃)=CH₂ group | H | 375.2 | ** |

TABLE-continued

| Example No. | X | W | R | R' | MS MH+ | Activity |
|---|---|---|---|---|---|---|
| 166. | H | NH | (2-oxotetrahydrofuran-3-yl, t-Bu linker) | H | 405.2 | ** |
| 167. | H | NH | (3-methylpentan-2-yl, gem-dimethyl) | H | 377.3 | ** |
| 168. | H | NH | (CH2)3NEt2 with methyl branches | H | 462.4 | *** |
| 169. | H | NH | quinuclidinyl | H | 430.3 | *** |
| 170. | H | NH | CH2CH2CHO | H | 377.2 | * |
| 171. | H | NH | 4-hydroxypentyl with gem-dimethyl | H | 393.3 | *** |
| 172. | H | NH | 2-(5-methoxy-1H-indol-3-yl)ethyl with gem-dimethyl | H | 494.3 | ** |
| 173. | H | NH | 2,3-dimethylbutyl with gem-dimethyl | H | 391.3 | ** |

TABLE-continued

| Example No. | X | W | R | R' | MS MH+ | Activity |
|---|---|---|---|---|---|---|
| 174. | H | NH | (isobutyl methyl ether group) | H | 393.2 | ** |
| 175. | H | NH | (ethyl 3-methylbutanoate group) | H | 435.2 | ** |
| 176. | H | — | $CH_2CH_2CH_2NEt_2$ | H | 419.4 | *** |
| 177. | H | NH | nBu | H | 377.4 | ** |
| 178. | H | NH | $CH_2CH_2SMe$ | H | 395.3 | ** |
| 179. | H | NH | (morpholinopropyl group) | H | 448.4 | *** |
| 180. | H | NH | (2-fluoro-6-chlorobenzylthiopropyl group) | H | 523.3 | * |
| 181. | H | NH | (3-methylheptyl group) | H | 419.4 | * |
| 182. | H | NH | (N-Boc-aminopropyl group) | H | 464.3 | ** |
| 183. | H | NH | (1-methylpiperidin-4-yl group) | H | 418.4 | *** |
| 184. | H | NH | (2-(pyridin-4-yl)ethyl group) | H | 426.3 | ** |

TABLE-continued

| Example No. | X | W | R | R' | MS MH+ | Activity |
|---|---|---|---|---|---|---|
| 185. | H | NH | (CH₂N(CH₃)₂ on neopentyl) | H | 434.4 | *** |
| 186. | H | NH | (neopentyl-CH₂-CH₂-2-methylpiperidinyl) | H | 460.4 | *** |
| 187. | H | NH | CH(Et)₂ | H | 391.4 | ** |
| 188. | H | NH | CH₂CH₂CH₂CH₂Ph | H | 453.4 | * |
| 189. | H | NH | (diethyl glutarate-like) | H | 507.5 | ** |
| 190. | H | NH | (4-hydroxycyclohexyl on t-Bu) | H | 419.4 | ** |
| 191. | H | NH | (trimethylammonium on neopentyl) | H | 406.4 | ?? |
| 192. | H | NH | (ethyl ester chain) | H | 435.4 | * |
| 193. | H | NH | (CH₂NHCH₂Ph on neopentyl) | H | 454.5 | *** |
| 194. | H | NH | (cyclohexyl-CH(CH₃) on t-Bu) | H | 431.5 | * |

TABLE-continued
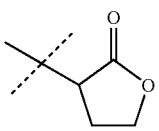
| Example No. | X | W | R | R' | MS MH+ | Activity |
|---|---|---|---|---|---|---|
| 195. | H | NH | 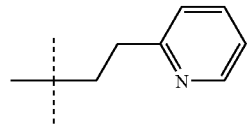 | H | 405.4 | ** |
| 196. | H | NH | 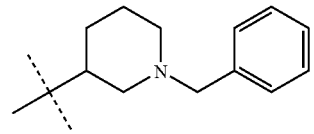 | H | 426.4 | ** |
| 197. | H | NH | 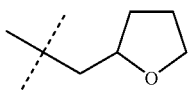 | H | 494.5 | ** |
| 198. | H | NH | 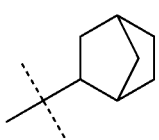 | H | 405.4 | ** |
| 199. | H | NH | 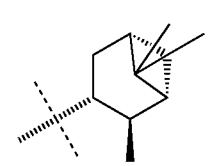 | H | 415.5 | * |
| 200. | H | NH | CH$_2$CH$_2$SCH$_2$Ph | H | 471.4 | * |
| 201. | H | NH | 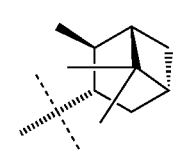 | H | 457.5 | * |
| 202. | H | NH | 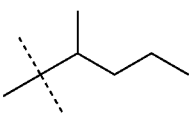 | H | 457.4 | * |
| 203. | H | NH |  | H | 391.4 | * |

TABLE-continued
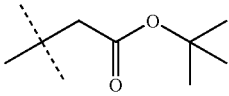
| Example No. | X | W | R | R' | MS MH+ | Activity |
|---|---|---|---|---|---|---|
| 204. | H | NH | CH₂cycloheptyl | H | 431.5 | * |
| 205. | H | NH | 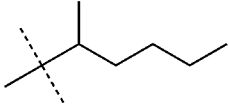 | H | 435.4 | * |
| 206. | H | NH | CH₂CH₂N(nBu)₂ | H | 476.5 | *** |
| 207. | H | NH | 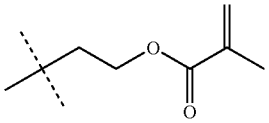 | H | 405.4 | ** |
| 208. | H | NH | CH₂CH₂OPh | H | 441.4 | ** |
| 209. | H | NH | 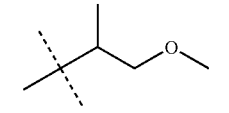 | H | 433.4 | * |
| 210. | H | NH | 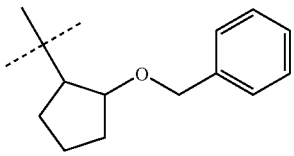 | H | 393.4 | *** |
| 211. | H | NH | 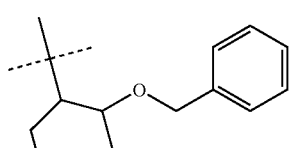 | H | 495.5 | * |
| 212. | H | NH | 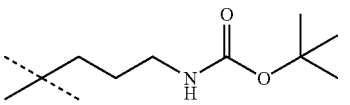 | H | 509.4 | * |
| 213. | H | NH |  | H | 478.5 | ** |

TABLE-continued

| Example No. | X | W | R | R' | MS MH+ | Activity |
|---|---|---|---|---|---|---|
| 214. | H | NH | 3-(1-benzyl)pyrrolidinyl | H | 480.4 | *** |
| 215. | H | NH | -CH₂C(O)O-n-butyl | H | 435.4 | * |
| 216. | H | NH | -CH₂C(O)O-n-pentyl | H | 449.4 | * |
| 217. | H | NH | -CH₂CH₂-(3-pyridyl) | H | 426.4 | ** |
| 218. | H | NH | -CH(CH₃)CH₂CH₂CH(CH₃)₂ | H | 419.5 | * |
| 219. | H | NH | -(CH₂)₆NHC(O)OCH₂Ph | H | 540.5 | ** |
| 220. | H | NH | -(CH₂)₅NHC(O)O-t-Bu | H | 492.5 | * |
| 221. | H | NH | -CH₂CH(Et)CH₂CH₃ | H | 405.5 | * |
| 222. | H | NH | -(CH₂)₅NHC(O)CH₃ | H | 434.4 | *** |

TABLE-continued

| Example No. | X | W | R | R' | MS MH+ | Activity |
|---|---|---|---|---|---|---|
| 223. | H | NH | *tert-butyl ester of 4,4-dimethylpentanoate* | H | 449.4 | ** |
| 224. | H | NH | *4-benzylpiperidine-N-propyl* | H | 522.5 | *** |
| 225. | H | NH | *3-(4-methoxyphenoxy)propyl* | H | 471.4 | * |
| 226. | H | NH | *2-indanyl* | H | 437.4 | * |
| 227. | H | NH | *3-[(2-trifluoromethylquinolin-4-yl)thio]propyl* | H | 576.4 | * |
| 228. | H | NH | *4-(pyrrolidin-1-yl)butyl* | H | 446.4 | *** |
| 229. | H | NH | *3-(pyrrolidin-1-yl)propyl* | H | 432.4 | *** |
| 230. | H | NH | *pyridin-4-ylmethyl* | H | 383.3 | * |

TABLE-continued

| Example No. | X | W | R | R' | MS MH+ | Activity |
|---|---|---|---|---|---|---|
| 231. | H | NH | (N-methyl tropane-like bicyclic amine) | H | 429.4 | *** |
| 232. | 6-F | — | CH₂CH₂CH₂NMe₂ | H | 409.4 | *** |
| 233. | 6-F | — | (alkyl-pyrrolidine) | H | 449.4 | *** |
| 234. | 6-F | — | (2,2,6,6-tetramethyl-1-methylpiperidinyl) | H | 477.4 | *** |
| 235. | 6-F | — | (alkyl-NH-cyclohexyl) | H | 463.4 | *** |
| 236. | H | — | (2,4-dimethoxybenzyl-like) | H | 456.4 | * |
| 237. | H | — | (4-NMe₂-benzyl-like) | H | 439.4 | *** |
| 238. | H | — | (tetrahydrofuran-2-ylmethyl) | H | 390.3 | ** |
| 239. | H | — | cycloButyl | H | 360.4 | ** |

TABLE-continued

| Example No. | X | W | R | R' | MS MH+ | Activity |
|---|---|---|---|---|---|---|
| 240. | H | — | 4-methoxybenzyl (neopentyl-linked) | H | 426.4 | *** |
| 241. | H | — | nButyl | H | 362.4 | ** |
| 242. | H | — | (furan-2-yl)methyl (neopentyl-linked) | H | 386.4 | *** |
| 243. | H | — | iPr | H | 348.4 | *** |
| 244. | H | — | cyclohexylmethyl | H | 402.4 | ** |
| 245. | H | — | nHeptyl | H | 404.4 | ** |
| 246. | H | — | Allyl | H | 346.3 | *** |
| 247. | H | — | $CH_2CH_2CH_2OMe$ | H | 378.4 | *** |
| 248. | H | — | 3-(trifluoromethyl)benzyl | H | 464.3 | * |
| 249. | H | — | 2-(trifluoromethyl)benzyl | H | 464.3 | * |
| 250. | H | — | 3-fluorobenzyl | H | 414.3 | *** |
| 251. | H | — | nPentyl | H | 376.4 | * |

TABLE-continued
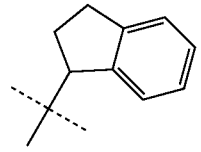
| Example No. | X | W | R | R' | MS MH+ | Activity |
|---|---|---|---|---|---|---|
| 252. | H | — | 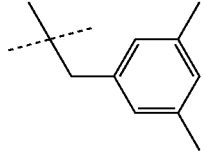 | H | 422.3 | * |
| 253. | H | — | 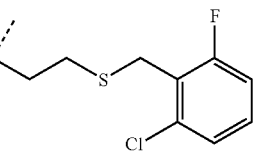 | H | 442.3 | * |
| 254. | H | — | 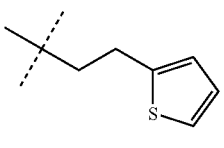 | H | 508.2 | * |
| 255. | H | — | 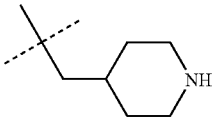 | H | 416.3 | * |
| 256. | H | — | 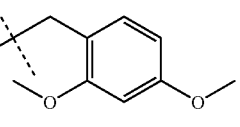 | H | 403.4 | ** |
| 257. | H | — | 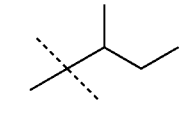 | H | 456.4 | * |
| 258. | H | — | 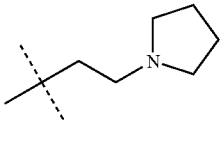 | H | 362.3 | ** |
| 259. | H | — |  | H |  | *** |

TABLE-continued
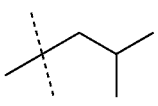
| Example No. | X | W | R | R' | MS MH+ | Activity |
|---|---|---|---|---|---|---|
| 260. | H | — | 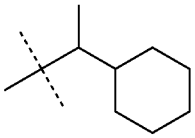 | H | | ** |
| 261. | H | NH | 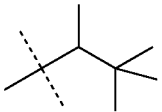 | H | 431.5 | * |
| 262. | H | NH | 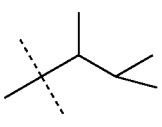 | H | 405.4 | * |
| 263. | H | NH | 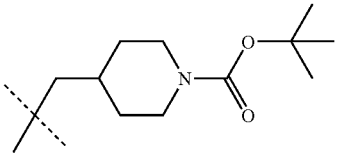 | H | 391.4 | ** |
| 264. | H | NH | 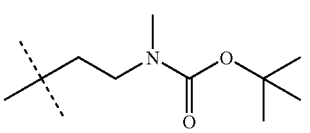 | H | 518.5 | * |
| 265. | H | NH | 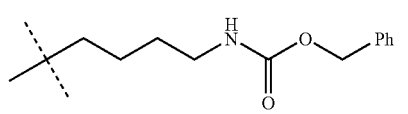 | H | | * |
| 266. | H | — | 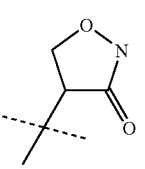 | H | 511.4 | *** |
| 267. | H | — |  | H | 391.4 | ** |

TABLE-continued

| Example No. | X | W | R | R' | MS MH+ | Activity |
|---|---|---|---|---|---|---|
| 268. | H | — | (3-(1H-indol-3-yl)propyl group) | H | 449.4 | ** |
| 269. | H | — | CH₂CH₂NHnPr | H | 391.4 | *** |
| 270. | H | — | CH₂CH₂Ph | H | 410.4 | * |
| 271. | H | — | CH₂CH₂CH₂CH₂CH₂CH₂NH₂ | H | 405.4 | *** |
| 272. | H | — | (3-cyclohexenylpropyl group) | H | 414.4 | * |
| 273. | H | — | CH₂CH₂CH₂OC₁₂H₂₅ | H | 532.6 | * |
| 274. | H | — | CH₂CH₂CH₂SCH₃ | H | 394.4 | *** |
| 275. | H | — | (ethyl 2-cyclopentanecarboxylate group) | H | 446.4 | ** |
| 276. | H | — | CH(Et)CH₂OCH₂Ph | H | 468.4 | ** |
| 277. | H | — | (tetrahydrofuran-2-one-3-yl group) | H | 390.3 | ** |
| 278. | H | — | (quinuclidin-3-yl group) | H | 415.4 | *** |
| 279. | H | — | CH₂CH₂NHnBu | H | 405.4 | *** |
| 280. | H | — | CH₂CH₂NHCH₂CH₂NEt₂ | H | 448.5 | *** |
| 281. | H | — | CH₂CH₂NHCH₂Ph | H | 439.4 | *** |
| 282. | H | NH | Et | H | 349.4 | *** |

TABLE-continued
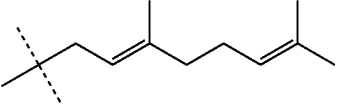
| Example No. | X | W | R | R' | MS MH+ | Activity |
|---|---|---|---|---|---|---|
| 283. | H | NH | 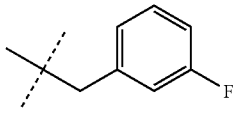 | H | 457.4 | * |
| 284. | H | NH | 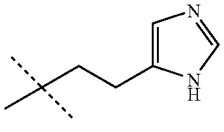 | H | 429.3 | * |
| 285. | H | NH | 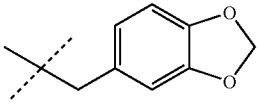 | H | 415.3 | *** |
| 286. | H | NH | 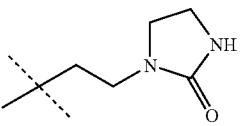 | H | 455.3 | * |
| 287. | H | NH | 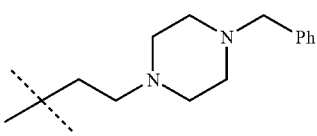 | H | 433.4 | *** |
| 288. | H | NH | 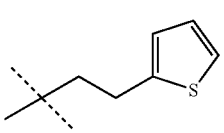 | H | 522.5 | *** |
| 289. | H | NH | 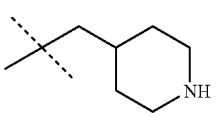 | H | 431.3 | ** |
| 290. | H | NH |  | H | 418.4 | *** |
| 291. | H | NH | CH$_2$CH$_2$CH$_2$Ph | H | 439.4 | * |

TABLE-continued
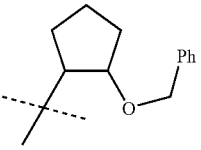
| Example No. | X | W | R | R' | MS MH+ | Activity |
|---|---|---|---|---|---|---|
| 292. | H | NH | 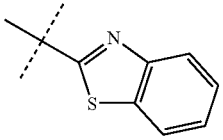 | H | 495.4 | * |
| 293. | H | NH | 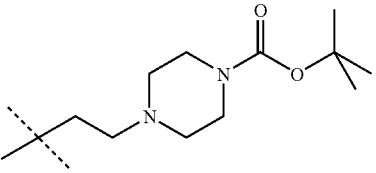 | H | 454.3 | * |
| 294. | H | NH | 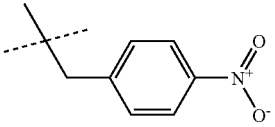 | H | 533.5 | ** |
| 295. | H | NH | CH₂CH₂CH₂NHCH₃ | H | 392.4 | *** |
| 296. | H | NH | 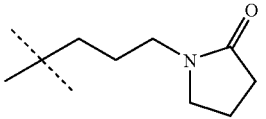 | H | 456.4 | * |
| 297. | H | NH | 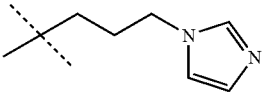 | H | 446.4 | ** |
| 298. | H | NH | 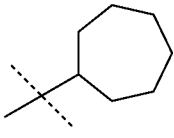 | H | 429.4 | *** |
| 299. | H | NH |  | H | 417.5 | * |

TABLE-continued
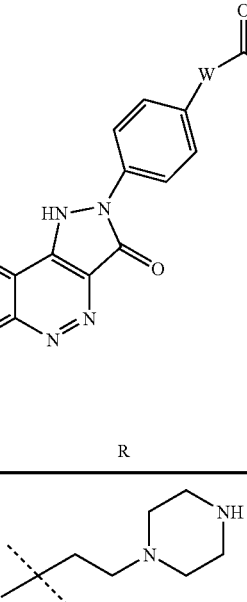
| Example No. | X | W | R | R' | MS MH+ | Activity |
|---|---|---|---|---|---|---|
| 300. | H | NH | 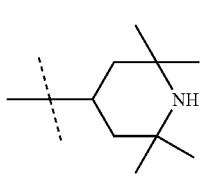 | H | 433.5 | *** |
| 301. | H | NH | 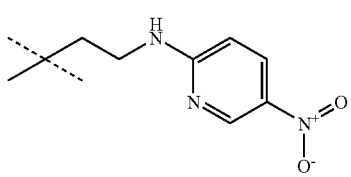 | H | 460.5 | *** |
| 302. | H | NH | 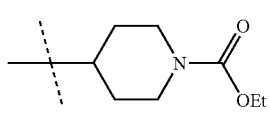 | H | 486.4 | * |
| 303. | H | NH | 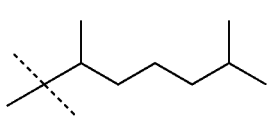 | H | 476.4 | * |
| 304. | H | NH | CH(CH$_3$)CH$_2$CH$_2$Ph | H | 453.4 | * |
| 305. | H | NH | 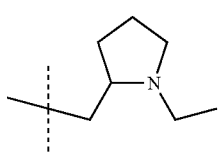 | H | 433.5 | * |
| 306. | H | NH | CH$_2$CH(OMe)$_2$ | H | 409.4 | *** |
| 307. | H | NH | CH$_2$CH(OEt)$_2$ | H | 437.5 | ** |
| 308. | H | NH | CH$_2$CH(CH$_3$)CH$_2$CH$_3$ | H | 391.4 | ** |
| 309. | H | NH | CH(CH$_3$)CH$_2$CH$_3$ | H | 377.4 | ** |
| 310. | H | NH |  | H | 432.4 | *** |
| 311. | H | — | CH$_2$CHF$_2$ | H | 370.4 | *** |
| 312. | H | — | CH$_2$CH$_2$CF$_3$ | H | 402.4 | *** |

TABLE-continued

| Example No. | X | W | R | R' | MS MH+ | Activity |
|---|---|---|---|---|---|---|
| 313. | H | — | (adamantyl) | H | 440.5 | ** |
| 314. | H | — | (1-ethynylcyclohexyl-methyl) | H | 412.5 | *** |
| 315. | H | — | (2-phenylcyclopropyl-methyl) | H | 422.5 | ** |
| 316. | H | — | (2-methylcyclohexyl-methyl) | H | 402.5 | ** |
| 317. | H | — | (2,3-dimethylcyclohexyl-methyl) | H | 416.5 | ** |
| 318. | H | — | (bornyl-methyl) | H | 442.5 | *** |
| 319. | H | — | tBu | H | 362.5 | *** |
| 320. | H | — | CH$_2$Si(CH$_3$)$_3$ | H | 392.5 | * |
| 321. | H | — | CH(CH$_3$)CH$_2$CH$_2$CH$_3$ | H | 376.5 | *** |
| 322. | H | — | CH(CH$_3$)CH$_2$CH$_2$CH$_2$CH$_3$ | H | 390.5 | *** |

TABLE-continued

| Example No. | X | W | R | R' | MS MH+ | Activity |
|---|---|---|---|---|---|---|
| 323. | 6-F | — | [4-(N-benzyl)piperidinyl] | H | 497.6 | *** |
| 324. | 6-F | NH | CH₂CH₂N(CH₃)₂ | H | 410.5 | *** |
| 325. | 8-F | — | [pyrrolidinyl-pentyl] | H | 449.3 | *** |
| 326. | 8-F | — | CH₂CH₂N(Et)₂ | H | 423.3 | *** |
| 327. | 8-F | — | [(N-methylpyrrolidin-2-yl)propyl] | H | 435.3 | *** |
| 328. | 8-F | — | [4-(N-benzyl)piperidinyl] | H | 497.3 | *** |
| 329. | 8-F | — | CH₂CH₂CH₂N(Bu)₂ | H | 493.4 | *** |
| 330. | 8-F | — | CH₂CH₂CH₂N(Et)₂ | H | 437.3 | *** |
| 331. | 8-F | — | [pyrrolidinyl-butyl] | H | 435.5 | *** |
| 332. | 8-F | — | [(2-methylpiperidinyl)propyl] | H | 463.3 | *** |
| 333. | 6-F | — | CH₂CH=CHCH₃ | H | 378.2 | *** |
| 334. | 6-F | — | [4-(N-phenacyl)piperidinyl] | H | 525.3 | *** |

TABLE-continued

| Example No. | X | W | R | R' | MS MH+ | Activity |
|---|---|---|---|---|---|---|
| 335. | 6-F | — | piperidine-N-CH₂CH₂OEt | H | 479.3 | *** |
| 336. | 6-F | — | piperidine-N-CH₂CH₂-cyclohexyl | H | 517.4 | *** |
| 337. | 6-F | — | piperidine-N-CH(Ph)CH₃ | H | 511.3 | *** |
| 338. | H | — | (CH₂)₄-morpholine | H | 447.3 | *** |
| 339. | H | — | (CH₂)₄-piperidine | H | 445.3 | *** |
| 340. | 6-F | — | CH₂C(=CH₂)CH₃ | H | 378.2 | *** |
| 341. | 6-F | — | CH₂CH₂NHnPr | H | 409.3 | *** |
| 342. | 6-F | — | CH₂CH₂N(Et)₂ | H | 423.3 | *** |
| 343. | 6-F | — | CH₂CH₂-(N-methylpyrrolidin-2-yl) | H | 435.3 | *** |
| 344. | 6-F | — | CH₂CH₂NHnBu | H | 423.3 | *** |
| 345. | 6-F | — | CH₂CH₂CH₂N(nBu)₂ | H | 493.4 | *** |
| 346. | 6-F | — | CH₂CH₂CH₂N(Et)₂ | H | 437.3 | *** |
| 347. | 6-F | — | CH₂CH₂NHCH₂Ph | H | 457.3 | *** |
| 348. | 6-F | — | CH₂CH₂CH₂NHiPr | H | 423.3 | *** |
| 349. | 6-F | — | 1-methylpiperidin-4-yl | H | 421.3 | *** |

TABLE-continued

| Example No. | X | W | R | R' | MS MH+ | Activity |
|---|---|---|---|---|---|---|
| 350. | 6-F | — | (4-morpholinylbutyl) | H | 451.3 | *** |
| 351. | 6-F | — | CH₂CH₂CH₂CH₂NH₂ | H | 395.3 | *** |
| 352. | 6-F | — | (4-pyrrolidinylbutyl) | H | 435.3 | *** |
| 353. | 6-F | — | (quinuclidinyl) | H | 433.3 | *** |
| 354. | 6-F | — | CH₂CH₂CH₂OnBu | H | 438.3 | *** |
| 355. | 6-F | — | CH₂CH₂CH₂NHMe | H | 395.3 | *** |
| 356. | 6-F | — | CH₂CH₂NHMe | H | 381.3 | *** |
| 357. | 6-F | — | CH₂CH₂NHEt | H | 395.3 | *** |
| 358. | 6-F | — | (4-(2-methylpiperidin-1-yl)butyl) | H | 463.4 | *** |
| 359. | 6-F | — | (2-methyl-3-(1H-indol-3-yl)propyl) | H | 481.3 | *** |
| 360. | 6-F | — | (2-(2-chlorophenyl)ethyl) | H | 462.2 | ** |
| 361. | 6-F | — | (2-(3,4-dimethoxyphenyl)ethyl) | H | 488.3 | *** |

TABLE-continued

| Example No. | X | W | R | R' | MS MH+ | Activity |
|---|---|---|---|---|---|---|
| 362. | 6-F | — | (4-methylphenyl)propyl | H | 442.3 | ** |
| 363. | 6-F | — | (4-chlorophenyl)propyl | H | 462.2 | ** |
| 364. | 6-F | — | (3-chlorophenyl)propyl | H | 462.2 | ** |
| 365. | 6-F | — | (3-bromophenyl)propyl | H | 506.2, 508.2 | * |
| 366. | 6-F | — | (2-methylphenyl)propyl | H | 442.3 | ** |
| 367. | 6-F | — | (3-methylphenyl)propyl | H | 442.3 | ** |
| 368. | 6-F | — | (2-bromophenyl)propyl | H | 506.2, 508.2 | ** |

TABLE-continued
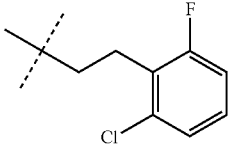
| Example No. | X | W | R | R' | MS MH+ | Activity |
|---|---|---|---|---|---|---|
| 369. | 6-F | — | 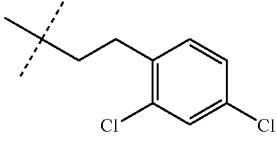 | H | 480.2 | ** |
| 370. | 6-F | — | 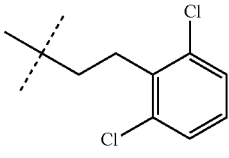 | H | 496.2 | ** |
| 371. | 6-F | — | 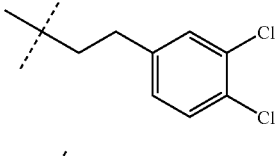 | H | 496.2 | ** |
| 372. | 6-F | — | 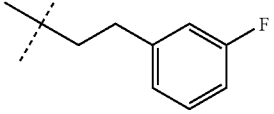 | H | 496.2 | ** |
| 373. | 6-F | — | 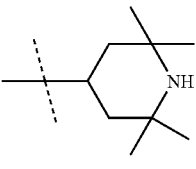 | H | 446.3 | ** |
| 374. | 6-F | — | 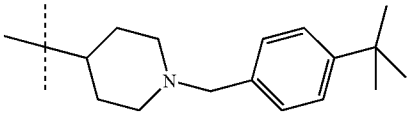 | H | 463.3 | *** |
| 375. | 6-F | — | tBu | H | 380.3 | *** |
| 376. | 6-F | — | $CH_2CHF_2$ | H | 388.2 | *** |
| 377. | 6-F | — | $CH_2CH=CH_2$ | H | 364.2 | *** |
| 378. | 6-F | — |  | H | 553.4 | *** |

TABLE-continued

| Example No. | X | W | R | R' | MS MH+ | Activity |
|---|---|---|---|---|---|---|
| 379. | 6-F | — | (4-piperidinyl-N-CH2-3,5-dimethylphenyl) | H | 524.4 | ** |
| 380. | 6-F | — | (4-piperidinyl-N-CH2-4-SO2Me-phenyl) | H | 575.3 | *** |
| 381. | 8-F | — | CH₂CH₂CH₂N(Me)₂ | H | 409.3 | *** |
| 382. | 8-F | — | (CH2)3-NH-cyclohexyl (gem-dimethyl) | H | 463.3 | *** |
| 383. | 8-F | — | CH₂CH₂NHEt | H | 409.3 | *** |
| 384. | 8-F | — | CH₂CH₂NHBu | H | 423.3 | *** |
| 385. | 8-F | — | CH₂CH₂CH₂NHiPr | H | 423.3 | *** |
| 386. | 8-F | — | CH₂CH₂CH₂CH₂OH | H | 396.3 | *** |
| 387. | 9-F | — | CH₂CH₂CH₂N(Me)₂ | H | 409.2 | *** |
| 388. | 9-F | — | (CH2)4-pyrrolidinyl (gem-dimethyl) | H | 449.2 | *** |
| 389. | 9-F | — | (CH2)3-NH-cyclohexyl (gem-dimethyl) | H | 463.3 | *** |
| 390. | 9-F | — | 1,2,2,6,6-pentamethyl-4-piperidinyl | H | 477.3 | *** |
| 391. | 9-F | — | 1-methyl-4-piperidinyl (gem-dimethyl) | H | 421.2 | *** |

TABLE-continued
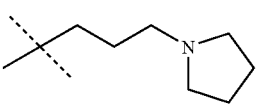
| Example No. | X | W | R | R' | MS MH+ | Activity |
|---|---|---|---|---|---|---|
| 392. | 9-F | — | CH₂CH₂CH₂N(Et)₂ | H | 437.2 | *** |
| 393. | 9-F | — | 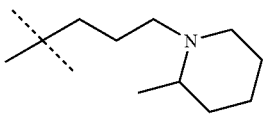 | H | 435.2 | *** |
| 394. | 9-F | — | 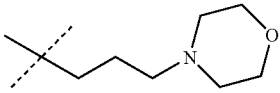 | H | 463.2 | *** |
| 395. | 9-F | — | CH₂CH₂CH₂NHiPr | H | 423.2 | *** |
| 396. | 9-F | — | CH₂CH₂CH₂NHMe | H | 395.2 | *** |
| 397. | 9-F | — | 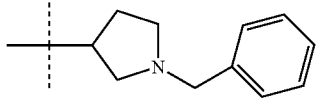 | H | 451.2 | *** |
| 398. | 9-F | — | CH₂CH₂CH₂N(nBu)₂ | H | 493.3 | *** |
| 399. | 9-F | — | 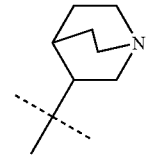 | H | 483.2 | *** |
| 400. | 9-F | — | tBu | H | 380.2 | *** |
| 401. | 9-F | — | 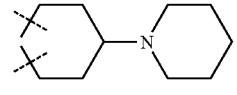 | H | 433.2 | *** |
| 402. | 9-F | — | 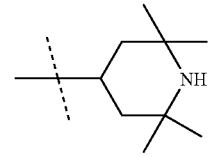 |  | 475.2 | ** |
| 403. | 9-F | — |  | H | 463.3 | *** |

TABLE-continued
| Example No. | X | W | R | R' | MS MH+ | Activity |
|---|---|---|---|---|---|---|
| 404. | 9-F | — | 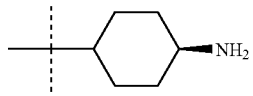 | H | 437.2 | *** |
| 405. | 9-F | — | 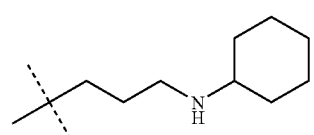 | H | 421.2 | *** |
| 406. | 8-Me | — | $CH_2CH_2CH_2N(Me)_2$ | H | 405.3 | *** |
| 407. | 8-Me | — | 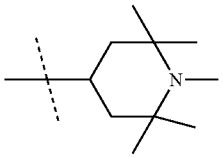 | H | 459.3 | *** |
| 408. | 8-Me | — | 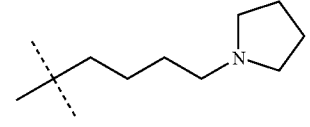 | H | 473.4 | *** |
| 409. | 8-Me | — | 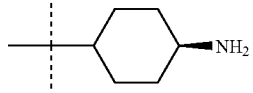 | H | 445.3 | *** |
| 410. | 6-F | — | 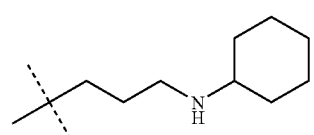 | H | 421.3 | *** |
| 411. | 6-Cl | — | $CH_2CH_2CH_2N(Me)_2$ | H | 425.3 | *** |
| 412. | 6-Cl | — | 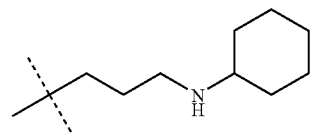 | H | 479.2 | *** |

TABLE-continued

[Structure diagram: benzo-fused pyrazolo-cinnoline core with X substituent, NH-N, C=O, attached to phenyl-W-C(=O)-N(R)(R')]

| Example No. | X | W | R | R' | MS MH+ | Activity |
|---|---|---|---|---|---|---|
| 413. | 6-Cl | — | [CH₂C(Me)₂-(CH₂)₃-pyrrolidinyl] | H | 465.3 | *** |
| 414. | 6,8-diF | — | CH₂CH₂CH₂N(Me)₂ | H | 427.3 | *** |
| 415. | 6,8-diF | — | [CH₂C(Me)₂-CH₂CH₂-NH-cyclohexyl] | H | 481.3 | *** |
| 416. | 6,8-diF | — | [CH₂C(Me)₂-(CH₂)₃-pyrrolidinyl] | H | 467.2 | *** |
| 417. | 6-F | — | [CH₂C(Me)₂-(CH₂)₃-NH-cyclohexyl] | H |  | *** |
| 418. | 8-MeO | — | CH₂CH₂CH₂NHMe | H | 407.2 | *** |
| 419. | 6-F | — | [CH₂C(Me)₂-(CH₂)₃-thiomorpholinyl] | H | 481.2 | *** |
| 420. | 6-F | — | [CH₂-C(Me)₂-CH₂-NMe₂] | H | 437.2 | *** |
| 421. | 6-F | — | [cyclohexyl-N-piperidinyl, gem-disubstituted] |  | 475.2 | ** |
| 422. | 6-F | — | CH₂CF₂CF₂CF₃ | H | 456.1 | *** |
| 423. | 6-F | — | CH₂CH₂CF₃ | H | 420.1 | *** |

TABLE-continued

| Example No. | X | W | R | R' | MS MH+ | Activity |
|---|---|---|---|---|---|---|
| 424. | 6-F | — | (cyclobutylmethyl-like, CH(CH₃) linked to cyclobutyl) | H | 378.1 | *** |
| 425. | 6-F | — | (CH(CH₃) linked to cyclopentyl) | H | 392.2 | *** |
| 426. | 6-F | — | CH₂CH₂F | H | 370.1 | *** |
| 427. | 8-F | — | (2,2,6,6-tetramethyl-1-methylpiperidin-4-yl) | H | 477.3 | *** |
| 428. | 6,9-diF | — | CH₂CH₂CH₂NHMe | H | 413.2 | *** |
| 429. | 6,9-diF | — | (CH₂)₃NH-cyclohexyl | H | 481.3 | *** |
| 430. | 6,9-diF | — | (CH₂)₄-pyrrolidinyl | H | 467.2 | *** |
| 431. | 6,9-diF | — | (2,2,6,6-tetramethyl-1-methylpiperidin-4-yl methyl) | H | 495.3 | *** |
| 432. | 6-F | — | CH₂CH₂CH₂CH₂N(Et)Me | H | 437.2 | *** |
| 433. | 6-F | — | CH₂CH₂CH₂CH₂N(Et)₂ | H | 451.3 | *** |
| 434. | 6-F | — | (CH₂)₄-morpholinyl | H | 465.2 | *** |
| 435. | 6-F | — | CH₂CH₂CH₂CH₂N(Me)CH₂CH=CH₂ | H | 449.2 | *** |

TABLE-continued
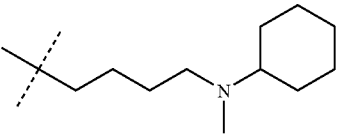
| Example No. | X | W | R | R' | MS MH+ | Activity |
|---|---|---|---|---|---|---|
| 436. | 6-F | — | 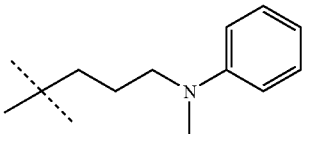 | H | 491.4 | *** |
| 437. | 6-F | — | CH$_2$CH$_2$CH$_2$CH$_2$F | H | 398.2 | *** |
| 438. | 6-F | — | 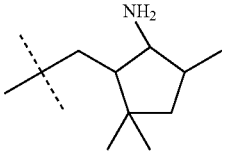 | H | 471.2 | ** |
| 439. | 6-F | — | 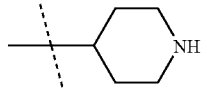 | H | 463.3 | *** |
| 440. | 6-F | — | 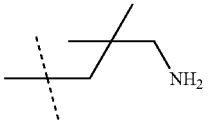 | H | 407.2 | *** |
| 441. | 6-F | — | 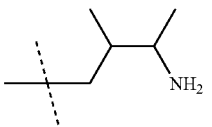 | H | 409.3 | *** |
| 442. | 6-F | — | CH$_2$CH$_2$CH$_2$NHnPr | H | 423.2 | *** |
| 443. | 6-F | — | 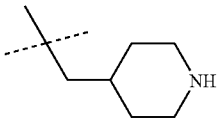 | H | 409.2 | *** |
| 444. | 6-F | — |  | H | 421.1 | *** |
| 445. | 6-F | — | CH$_2$CH$_2$CH$_2$NH$_2$ | H | 381.2 | *** |
| 446. | 8-Cl | — | CH$_2$CH$_2$CH$_2$N(Me)$_2$ | H | 425.2 | *** |

TABLE-continued

| Example No. | X | W | R | R' | MS MH+ | Activity |
|---|---|---|---|---|---|---|
| 447. | 8-Cl | — | (4-substituted-2,2,6,6-tetramethylpiperidinyl group) | H | 493.2 | *** |
| 448. | 8-Cl | — | (N-cyclohexylaminobutyl group) | H | 479.3 | *** |
| 449. | 8-Cl | — | (pyrrolidinyl-butyl group) | H | 465.2 | *** |
| 450. | 6-F | — | Et | H | 352.2 | *** |
| 451. | 6-F | — | (azepanyl-propyl group) | H | 463.3 | *** |
| 452. | 6-F | — | Et | nPr | 394.2 | ** |
| 453. | 6-F | — | (1-ethyl-piperidin-4-yl group) | H | 435.2 | *** |
| 454. | 6-F | — | (2-methyl-piperidinyl-butyl group) | H | 477.3 | *** |
| 455. | 6-F | — | CH₂tBu | H | 394.2 | *** |
| 456. | 6-F | — | (1-cyclohexylmethyl-piperidin-4-yl group) | H | 503.3 | *** |

TABLE-continued

| Example No. | X | W | R | R' | MS MH+ | Activity |
|---|---|---|---|---|---|---|
| 457. | 6-F | — | 4-(3-phenylpropyl)piperazin-1-yl piperidinyl group | H | 539.3 | *** |
| 458. | 6-F | — | 4,4-difluoro-2-propylpiperidinyl | H | 471.2 | *** |
| 459. | 6-F | — | CH₂CH₂CH₂CH₂N(CH₂CH=CH₂)₂ | H | 475.3 | *** |
| 460. | 6-F | — | 2,6-dimethylmorpholinyl-alkyl | H | 493.3 | *** |
| 461. | 6-F | — | 2,6-dimethyltetrahydropyranyl | | 422.2 | *** |
| 462. | 6-F | — | azepan-1-yl-alkyl | H | 477.3 | *** |
| 463. | 6-F | — | cycloheptyl | | 406.2 | *** |
| 464. | 6-F | — | 4-methylpiperidin-1-yl-alkyl | H | 477.3 | *** |
| 465. | 6-F | — | 4-methylcyclohexyl | | 406.2 | *** |

TABLE-continued

| Example No. | X | W | R | R' | MS MH+ | Activity |
|---|---|---|---|---|---|---|
| 466. | 6-F | — | (2,2,6-trimethylbicyclic amine structure) | H | 519.2 | *** |
| 467. | 6-F | — | CH₂CF₂CF₂H | H | 438.1 | *** |
| 468. | 6-F | — | (N-ethyl, N-cyclopropylmethyl amine) | H | 491.3 | *** |
| 469. | 6-F | — | (N-allyl, N-cyclopentyl amine) | H | 503.3 | *** |
| 470. | 6-F | — | (4-CF₃-piperidinyl) | H | 531.3 | *** |
| 471. | 6-F | — | (4-(3-fluoropropyl)piperidinyl) | H | 481.2 | *** |
| 472. | 6-F | — | (4-dimethylaminocyclohexyl) | H | 449.3 | *** |
| 473. | 8-F | — | CH₂CF₂H | H | 388.1 | *** |
| 474. | 6-F | — | allyl | allyl | 404.2 | ** |
| 475. | 6-F | — | CH₂CH₂CF=CF₂ | H | 432.1 | ** |
| 476. | 6-F | — | (N,N-diisobutyl amine) | H | 507.3 | *** |

TABLE-continued
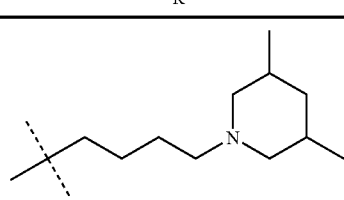
| Example No. | X | W | R | R' | MS MH+ | Activity |
|---|---|---|---|---|---|---|
| 477. | 6-F | — | 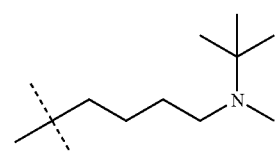 | H | 491.3 | *** |
| 478. | 6-F | — | 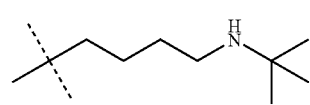 | H | 465.3 | *** |
| 479. | 6-F | — | 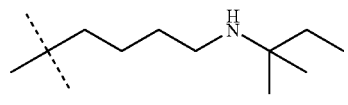 | H | 451.2 | *** |
| 480. | 6-F | — | 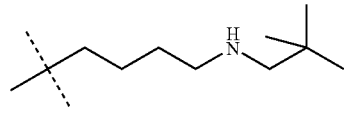 | H | 465.2 | *** |
| 481. | 6-F | — | 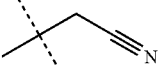 | H | 465.2 | *** |
| 482. | 6-F | — | 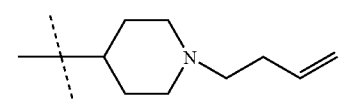 | H | 363.1 | *** |
| 483. | 6-F | — | 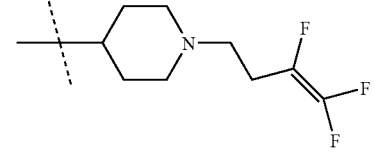 | H | 461.3 | *** |
| 484. | 6-F | — | 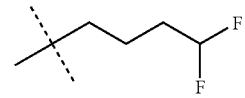 | H | 515.3 | *** |
| 485. | 6-F | — |  | H | 416.2 | *** |

TABLE-continued

| Example No. | X | W | R | R' | MS MH+ | Activity |
|---|---|---|---|---|---|---|
| 486. | 6-F | — | (CH₂ group with C≡N) | H | 377.1 | *** |
| 487. | 6-F | — | C(CH₂OH)₃ | H | 428.2 | *** |
| 488. | 6-F | — | (pyrrolidine substituent) | H | 393.1 | *** |
| 489. | 6-F | — | (N-methyl azepane) | | 421.2 | *** |
| 490. | 6-F | — | (azepane NH) | | 407.1 | *** |
| 491. | 6-F | — | CH₂CONH₂ | H | 381.2 | *** |
| 492. | 6-F | — | (4-(difluoromethylene)cyclohexyl) | H | 454.1 | *** |
| 493. | 6-F | — | (fluoroalkyl) | H | 398.1 | *** |
| 494. | 6-F | — | (cycloheptyl) | | 420.2 | ** |
| 495. | 6-F | — | (decalinyl) | | 446.2 | |
| 496. | 6-F | — | (decalinyl) | | 446.2 | |

TABLE-continued

| Example No. | X | W | R | R' | MS MH+ | Activity |
|---|---|---|---|---|---|---|
| 497. | 6-F | — | (2-methyl-1-phenyl-propyl with CN) | H | 439.1 | ** |
| 498. | 6-F | — | iPr, dimethyl, CN group | H | 419.2 | *** |
| 499. | 6-F | — | cyclohexyl with NH₂ | H | 421.2 | *** |
| 500. | 6,9-diF | — | CH₂CHF₂ | H | 406.2 | *** |
| 501. | 6-F | — | cyclohexyl-OH | H | 422.2 | *** |
| 502. | 6-F | — | alkyl-OH | H | 396.2 | *** |
| 503. | 6-F | — | cycloheptyl-OH | H | 450.2 | ** |
| 504. | 6-F | — | cyclohexyl-OH | H | 436.2 | ** |
| 505. | 6-F | — | CH₂CH₂NHCH₂CH₂OH | H | 411.2 | *** |

TABLE-continued

| Example No. | X | W | R | R' | MS MH+ | Activity |
|---|---|---|---|---|---|---|
| 506. | 6-F | — | (2-hydroxycycloheptyl-methyl) | H | 464.2 | ** |
| 507. | 6-F | — | CH(CH₂OH)₂ | H | 398.1 | *** |
| 508. | 6-F | — | CH(CH₃)CH₂OH | H | 382.1 | *** |
| 509. | 6-F | — | CH(CH₂CH₃)CH₂OH | H | 396.2 | *** |
| 510. | 6-F | — | (1-methyl-2-hydroxyindanyl) | H | 456.2 | ** |
| 511. | 6-F | — | (2,2-dimethyl-3-hydroxy-1-(4-hydroxyphenyl)propyl) | H | 474.1 | ** |
| 512. | 6-F | — | (3,3-dimethyl-1-hydroxy-1,2-diphenylbutyl) | H | 520.2 | * |
| 513. | 6-F | — | (2-methyl-3-hydroxy-2-(hydroxymethyl)-1-phenylpropyl) | H | 474.1 | ** |

TABLE-continued

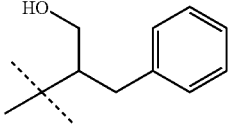

| Example No. | X | W | R | R' | MS MH+ | Activity |
|---|---|---|---|---|---|---|
| 514. | 6-F | — | 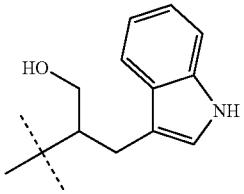 | H | 458.2 | *** |
| 515. | 6-F | — | 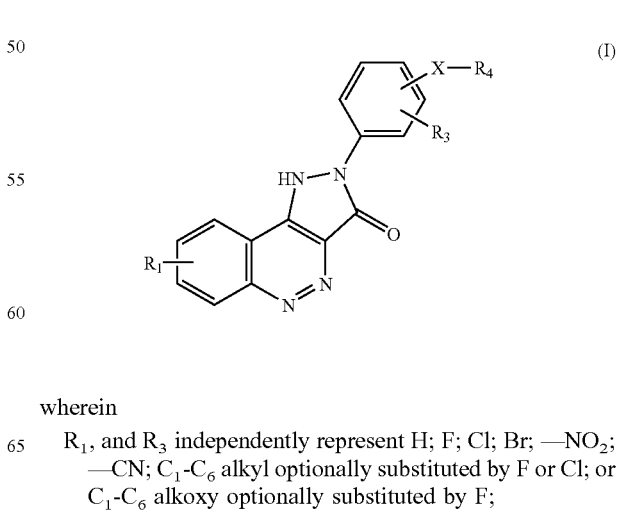 | H | 497.2 | ** |
| 516. | 6-F | — | C(CH₃)₂CH₂OH | H | 396.2 | * |
| 517. | 6-F | — | C CH₃(CH₂OH)₂ | H | 412.1 | *** |

Examples of the result of testing the above compounds in the assay for inhibition of production of interleukin-2 (IL-2) by human Jurkat T cells, described above, are as follows:

| Example No (see table) | Compound Concentration (µM) | Percentage Inhibition (relative to DMSO = 0%) |
|---|---|---|
| 478 | 10 | 56.0 |
| 376 | 10 | 56.7 |
| 353 | 10 | 77.4 |
| 429 | 10 | 58.8 |
| 349 | 10 | 79.5 |
| 68 | 10 | 71.7 |
| 235 | 10 | 59.3 |
| 288 | 30 | 72 |
| 162 | 30 | 54.4 |
| 350 | 10 | 74.2 |
| 381 | 10 | 48.5 |
| 442 | 10 | 58.9 |
| 482 | 10 | 39.2 |
| 472 | 10 | 58.4 |
| 453 | 10 | 55.7 |
| 53 | 30 | 63.8 |

The invention claimed is:

1. A compound of formula (I) or a pharmaceutically or veterinarily acceptable salt or hydrate thereof:

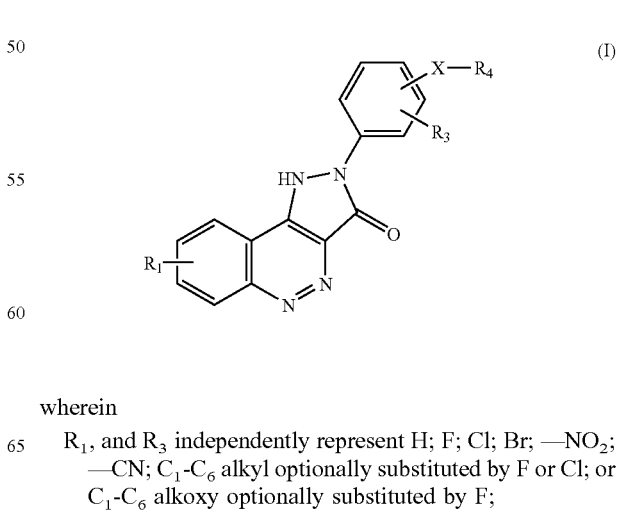

wherein $R_1$, and $R_3$ independently represent H; F; Cl; Br; —NO₂; —CN; $C_1$-$C_6$ alkyl optionally substituted by F or Cl; or $C_1$-$C_6$ alkoxy optionally substituted by F;

R$_4$ represents a carboxylic acid group (—COOH) or an ester thereof, or —C(=O)NR$_6$R$_7$, —NR$_7$C(=O)R$_6$, —NR$_7$C(=O)OR$_6$, —NHC(=O)NR$_7$R$_6$ or —NHC(=S)NR$_7$R$_6$ wherein R$_6$ represents H, or a radical of formula -(Alk)$_m$-Q wherein m is 0 or 1

Alk is an optionally substituted divalent straight or branched C$_1$-C$_{12}$ alkylene, or C$_2$-C$_{12}$ alkenylene, or C$_2$-C$_{12}$ alkynylene radical or a divalent C$_3$-C$_{12}$ carbocyclic radical, any of which radicals may contain one or more —O—, —S— or —N(R$_8$)— links wherein R$_8$ represents H or C$_1$-C$_4$ alkyl, C$_3$-C$_4$ alkenyl, C$_3$-C$_4$ alkynyl, or C$_3$-C$_6$ cycloalkyl, and Q represents H; —NR$_9$R$_{10}$ wherein R$_9$ and R$_{10}$ independently represents H; C$_1$-C$_4$ alkyl; C$_3$-C$_4$ alkenyl; C$_3$-C$_4$ alkynyl; C$_3$-C$_6$ cycloalkyl; an ester group; an optionally substituted carbocyclic or heterocyclic group; or R$_9$ and R$_{10}$ form a ring when taken together with the nitrogen to which they are attached, which ring is optionally substituted; and R$_7$ represents H or C$_1$-C$_6$ alkyl; or when taken together with the atom or atoms to which they are attached R$_6$ and R$_7$ form an optionally substituted monocyclic heterocyclic ring having 5, 6 or 7 ring atoms; and X represents a bond or a divalent radical of formula -(Z)$_n$-(Alk)- or -(Alk)-(Z)$_n$-wherein Z represents —O—, —S— or —NH—, Alk is as defined in relation to R$_6$ and n is 0 or 1.

2. A compound as claimed in claim 1 wherein the radical R$_4$X— is in the 4-position of the phenyl ring.

3. A compound as claimed in claim 1 wherein X is a bond.

4. A compound as claimed in claim 1 wherein R$_3$ is hydrogen.

5. A compound as claimed in claim 1 wherein R$_1$ is hydrogen or fluoro.

6. A compound as claimed in claim 1 wherein R$_4$ represents —C(=O)NR$_6$R$_7$.

7. A compound as claimed in claim 1 wherein R$_4$ represents —NHC(=O)NR$_7$R$_6$.

8. A compound as claimed in claim 7 wherein R$_6$ is a quinuclidinyl radical.

9. A compound as claimed in claim 1 wherein R$_6$ represents a radical of formula -(Alk)$_m$-Q wherein m is 1 and the divalent radical Alk contains 3 or 4 carbon atoms and is unsubstituted, and Q represents —NR$_9$R$_{10}$ wherein R$_9$ and R$_{10}$ independently represent H; C$_1$-C$_4$ alkyl; C$_3$-C$_4$ alkenyl; C$_3$-C$_4$ alkynyl; C$_3$-C$_6$ cycloalkyl; an ester group; an optionally substituted carbocyclic or heterocyclic group; or form a ring when taken together with the nitrogen to which they are attached, which ring is optionally substituted.

10. A compound as claimed in claim 6 wherein R$_7$ is hydrogen.

11. A compound as claimed in claim 1 wherein Q represents H; —CF$_3$; —OH; —SH; —NR$_8$R$_8$wherein each R$_8$ independently represents H; C$_1$-C$_4$ alkyl; C$_3$-C$_4$ alkenyl; C$_3$-C$_4$ alkynyl; C$_3$-C$_6$ cycloalkyl; an ester group; an optionally substituted aryl, aryloxy, cycloalkyl, cycloalkenyl or heterocyclic group; or form a ring when taken together with the nitrogen to which they are attached; and R$_7$ represents H or C$_1$-C$_6$ alkyl; or when taken together with the atom or atoms to which they are attached R$_6$ and R$_7$ form a monocyclic heterocyclic ring having 5, 6 or 7 ring atoms.

12. A compound as claimed in claim 11 wherein R$_4$ represents a carboxylic acid group (—COOH) or an ester group of formula —COOR wherein R is methyl, ethyl, n- or iso-propyl, n-, sec- or tert-butyl or benzyl.

13. A compound as claimed in claim 11 wherein R$_6$ represents a radical of formula -(Alk)$_m$-Q wherein m is 1, Alk is —CH$_2$—, —CH$_2$CH$_2$—, —CH$_2$CH$_2$CH$_2$—, or —CH$_2$CH(CH$_3$)CH$_2$—, or a divalent cyclopropylene, cyclopentylene or cyclohexylene radical, optionally substituted by —OH, oxo, CF$_3$, methoxy or ethoxy, and Q represents hydrogen; —NR$_8$R$_8$ wherein each R$_8$ may be the same or different and selected from hydrogen, methyl, ethyl, n- or isopropyl or tert-butyl; a methyl, ethyl or benzyl ester; or an optionally substituted phenyl, phenoxy, cyclopentyl, cyclohexyl, furyl, thienyl, piperidyl, or piperazinyl group.

14. A compound as claimed in claim 11 wherein R$_7$ represents methyl, ethyl, n- or iso-propyl, n-, sec- or tert-butyl; or when taken together with the atom or atoms to which they are attached R$_6$ and R$_7$ form a monocyclic heterocyclic ring having 5, 6 or 7 ring atoms.

15. A compound as claimed in claim 11 wherein R$_1$ is H, F, Cl, methyl, methoxy, or methylenedioxy.

16. A compound as claimed in claim 11 wherein R$_1$ is F, in the 6-position of the 3-oxo-1,3-dihydro-2H-pyrazolo[4,3-c]cinnolin-2-yl ring system.

17. A compound as claimed in claim 11 wherein R$_3$ is H, F, Cl, methyl, methoxy, or methylenedioxy.

18. A compound as claimed in claim 11 wherein X is a bond, or a —CH$_2$— or —CH$_2$CH$_2$— radical.

19. A compound of formula (IC) or a pharmaceutically or veterinarily acceptable salt or hydrate thereof:

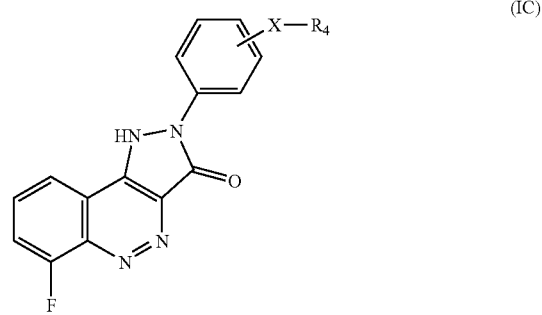

(IC)

wherein X is a bond, or a —CH$_2$— or —CH$_2$CH$_2$— radical and R$_4$ is a carboxylic acid group (—COOH), an ester group of formula —COOR wherein R is methyl, ethyl, n- or iso-propyl, n-, sec- or tert-butyl or benzyl, or —NHC(=O)NR$_6$R$_7$ wherein R$_6$ represents H, or a radical of formula -(Alk)$_m$-Q wherein m is 0 or 1

Alk is an optionally substituted divalent straight or branched C$_1$-C$_{12}$ alkylene, or C$_2$-C$_{12}$ alkenylene, or C$_2$-C$_{12}$ alkynylene radical or a divalent C$_3$-C$_{12}$ carbocyclic radical, any of which radicals may contain one or more —O—, —S— or —N(R$_8$)— links wherein R$_8$ represents H or C$_1$-C$_4$ alkyl, C$_3$-C$_4$ alkenyl, C$_3$-C$_4$ alkynyl, or C$_3$-C$_6$ cycloalkyl, and Q represents H; —NR$_9$R$_{10}$ wherein R$_9$ and R$_{10}$ independently represents H; C$_1$-C$_4$alkyl; C$_3$-C$_4$ alkenyl, C$_3$-C$_4$alkynyl; C$_3$-C$_6$ cycloalkyl; an ester group; an optionally substituted carbocyclic or heterocyclic group; or R$_9$ and R$_{10}$ form a ring when taken together with the nitrogen to which they are attached, which ring is optionally substituted; and $R_7$ represents H or $C_1$-$C_6$alkyl; or when taken together with the atom or atoms to which they are attached $R_6$ and $R_7$ form an optionally substituted monocyclic heterocyclic ring having 5, 6 or 7 ring atoms.

20. A compound as claimed in claim 18 wherein the radical $R_4X$— is in the 4-position of the phenyl ring.

21. A compound as claimed in claim 19 wherein X is a bond and $R_4$ is —C(═O)$NR_6R_7$.

22. The compound 4-(6-fluoro-3-oxo-1,3-dihydro-pyrazolo[4,3-c]cinnolin-2-yl)-N-(2,2-difluoro-ethylyl)-benzamide, of formula (A)

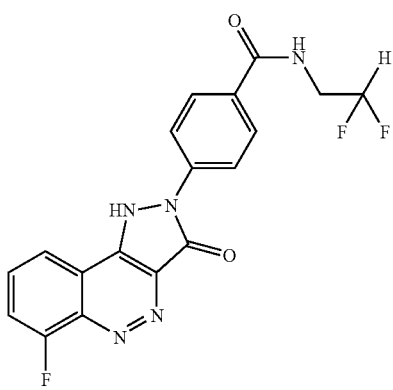
(A)

23. The compound N-[3-(tert-butyl-methyl-amino)-butyl]-4-(6-fluoro-3-oxo-1,3-dihydro-pyrazolo[4,3-c]cinnolin-2-yl)-benzamide, of formula (B):

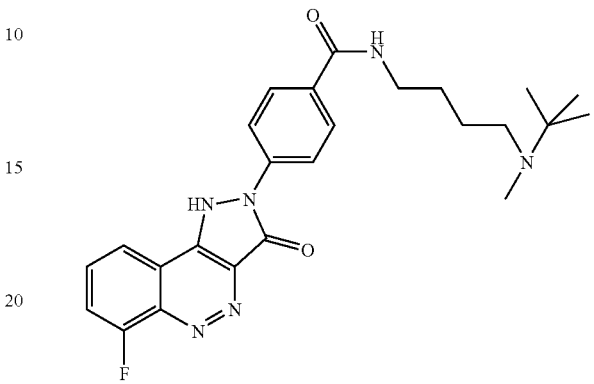
(B)

or a pharmaceutically or veterinarily acceptable salt or hydrate thereof.

24. A pharmaceutical or veterinary composition comprising a compound as claimed in claim 1 together with a pharmaceutically or veterinarily acceptable excipient or carrier.

* * * * *